United States Patent
Lee et al.

(10) Patent No.: US 11,530,228 B2
(45) Date of Patent: Dec. 20, 2022

(54) TETRACARBOXYLIC ACID DIANHYDRIDE AND METHOD FOR PREPARING THE SAME

(71) Applicants: SK Innovation Co., Ltd., Seoul (KR); SK ie technology Co., Ltd., Seoul (KR)

(72) Inventors: So Young Lee, Daejeon (KR); Jong Chan Kim, Daejeon (KR)

(73) Assignees: SK Innovation Co., Ltd., Seoul (KR); SK ie technology Co., Ltd., Seoul (KR)

( * ) Notice: Subject to any disclaimer, the term of this patent is extended or adjusted under 35 U.S.C. 154(b) by 0 days.

(21) Appl. No.: 17/371,471

(22) Filed: Jul. 9, 2021

(65) Prior Publication Data
US 2022/0009943 A1   Jan. 13, 2022

(30) Foreign Application Priority Data

Jul. 13, 2020 (KR) .................. 10-2020-0085873
Apr. 30, 2021 (KR) .................. 10-2021-0056240

(51) Int. Cl.
| | | |
|---|---|---|
| *C07D 495/20* | (2006.01) | |
| *C07D 493/10* | (2006.01) | |
| *C08J 5/18* | (2006.01) | |
| *C08G 73/10* | (2006.01) | |

(52) U.S. Cl.
CPC ......... *C07D 495/20* (2013.01); *C07D 493/10* (2013.01); *C08G 73/1067* (2013.01); *C08J 5/18* (2013.01); *C08J 2379/08* (2013.01)

(58) Field of Classification Search
None
See application file for complete search history.

(56) References Cited

U.S. PATENT DOCUMENTS

| | | |
|---|---|---|
| 5,061,809 A | 10/1991 | Angus, Jr. et al. |
| 11,014,932 B2 | 5/2021 | Ma et al. |
| 2009/0088551 A1 | 4/2009 | Yamashita et al. |

FOREIGN PATENT DOCUMENTS

| | | |
|---|---|---|
| JP | 200979165 A | 4/2009 |
| KR | 101787941 B1 | 10/2017 |
| WO | 2017221135 A1 | 12/2017 |

*Primary Examiner* — Samantha L Shterengarts
(74) *Attorney, Agent, or Firm* — The Webb Law Firm

(57) ABSTRACT

Provided are a novel tetracarboxylic acid dianhydride and a method for preparing the same. According to an exemplary embodiment of the present invention, a novel tetracarboxylic acid dianhydride appropriate for providing a polyimide film having high transparency and thermal resistance and having excellent thermal dimensional stability due to a substrate of which the stress is not increased even with a heat treatment at a high temperature and a method for preparing the same may be provided.

12 Claims, No Drawings

TETRACARBOXYLIC ACID DIANHYDRIDE AND METHOD FOR PREPARING THE SAME

CROSS-REFERENCE TO RELATED APPLICATIONS

This application claims priority to Korean Patent Application Nos. 10-2020-0085873 filed Jul. 13, 2020 and 10-2021-0056240 filed Apr. 30, 2021, the disclosures of which are hereby incorporated by reference in their entirety.

BACKGROUND OF THE INVENTION

Field of the Invention

The following disclosure relates to a tetracarboxylic acid dianhydride and a method for preparing the same.

Description of Related Art

Polyimide is conceived as a high thermal resistant, light, and flexible material. As a resin having excellent thermal dimensional stability in the polyimide field, aromatic polyimide is attracting attention. A polyimide film which is a molded body composed of aromatic polyimide having a rigid and linear chemical structure is widely used in the field requiring high thermal dimensional stability (low coefficient of linear thermal expansion) such as a base film of a flexible printed wiring board and an interlayer insulating film of a semiconductor. However, since aromatic polyimide having a low coefficient of linear thermal expansion is strongly colored by intramolecular conjugation and intramolecular/intermolecular charge transfer interaction, it is difficult to apply the aromatic polyimide in optical applications. In addition, since polyimide has a very strong intermolecular force, it lacks processability.

Meanwhile, a flexible device is manufactured by a method of applying a polyimide precursor composition on a conveyance board and curing the composition to form a film, completing a device by a subsequent process such as thin film transistor and organic film deposition, and then detaching the completed device from the conveyance board. The flexible device involving a high temperature process as such requires high thermal resistance at a high temperature. In particular, when a thin film transistor process using a low temperature polysilicon (LTPS) is used, a process temperature may be close to 500° C., and thus, the polyimide film which is formed as a film on a conveyance board should not undergo thermal decomposition by hydrolysis even during a process at high temperature and satisfy high thermal resistance. In addition, transparency after processing as well as storage stability should be secured.

Thus, development of a new polyimide which may satisfy high thermal resistance and also prevents hydrolysis to represent excellent chemical resistance and storage stability and improve optical/mechanical characteristics is needed for manufacturing a flexible device.

SUMMARY OF THE INVENTION

An embodiment of the present disclosures provides a novel tetracarboxylic acid dianhydride for providing a polyimide film having excellent thermal resistance and satisfying transparency and a low coefficient of linear thermal expansion and a method for preparing the same.

In one general aspect, a tetracarboxylic acid dianhydride represented by the following Chemical Formula 1 is provided:

[Chemical Formula 1]

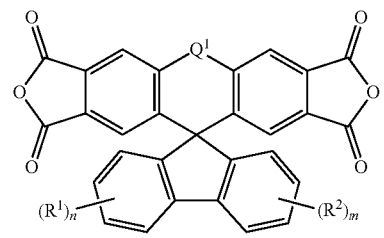

wherein $Q^1$ is a single bond, —C(=O)—, —C(=O)O—, —C(=O)NH—, —S—, —SO$_2$—, —NR'—, —CH$_2$—, or a combination thereof, wherein R' is hydrogen or C1-C10 alkyl;

$R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent to form a ring; and n and m are independently of each other an integer selected from 0 to 4, and when n and m are an integer of 2 or more, $R^1$ and $R^2$ may be the same as or different from each other.

The tetracarboxylic acid dianhydride may be a compound represented by the following Chemical Formula 2:

[Chemical Formula 2]

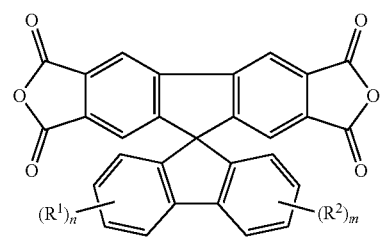

wherein $R^1$, $R^2$, n, and m are as defined in Chemical Formula 1 of

The tetracarboxylic acid dianhydride may be selected from compounds represented by the following Chemical Formulae 3 to 5:

[Chemical Formula 3]

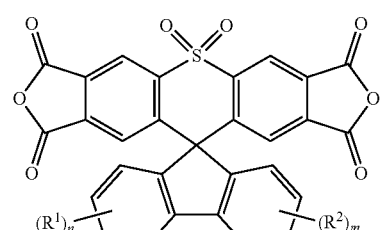

[Chemical Formula 4]

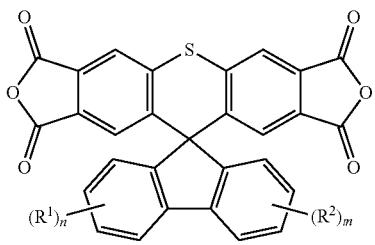

[Chemical Formula 5]

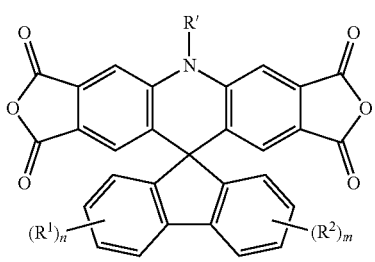

wherein

R¹, R², R', n, and m are as defined in the above Chemical Formula 1.

In the tetracarboxylic acid dianhydride, in Chemical Formula 1, R¹ and R² may be independently of each other a halogen, hydroxy, thiol, nitro, cyano, C1-C10 alkyl, C1-C10 alkoxy, C6-C20 aryl, C1-C10 haloalkyl, or C1-C10 haloalkoxy, and n and m may be independently of each other an integer selected from 0 to 2.

In the tetracarboxylic acid dianhydride, in Chemical Formula 1, R¹ and R² may be independently of each other a halogen, hydroxy, thiol, nitro, cyano, C1-C4 alkyl, C1-C4 alkoxy, C6-C18 aryl, C1-C4 haloalkyl, or C1-C4 haloalkoxy, and n and m may be independently of each other an integer selected from 0 to 2.

In the tetracarboxylic acid dianhydride, in Chemical Formula 1, R¹ and R² may be independently of each other a halogen, nitro, cyano, C1-C4 alkyl, C1-C4 alkoxy, C6-C12 aryl, C1-C4 haloalkyl, or C1-C4 haloalkoxy, and n and m may be independently of each other an integer selected from 0 to 2 and satisfy 0≤n+m≤2.

The tetracarboxylic acid dianhydride may be at least one or two or more selected from the following structures:

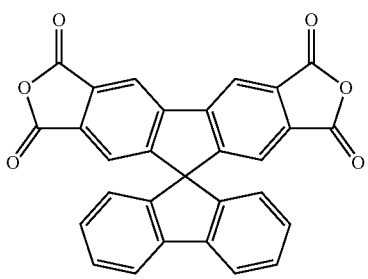

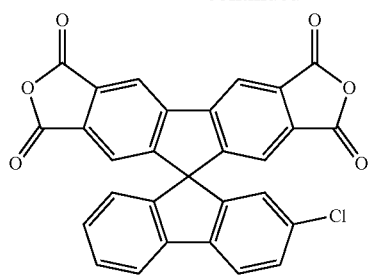

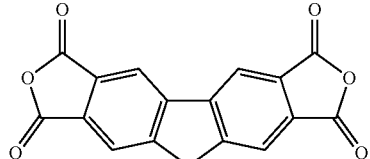

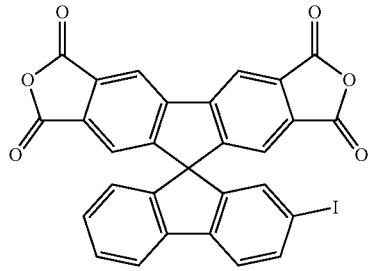

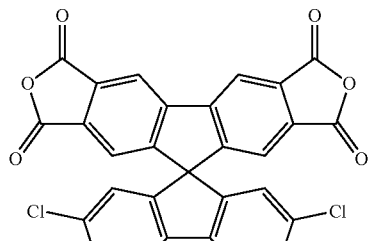

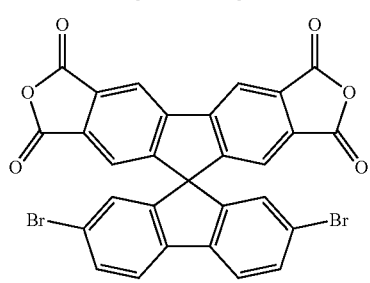

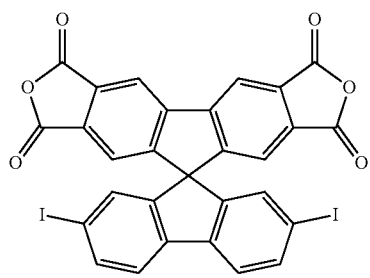

-continued
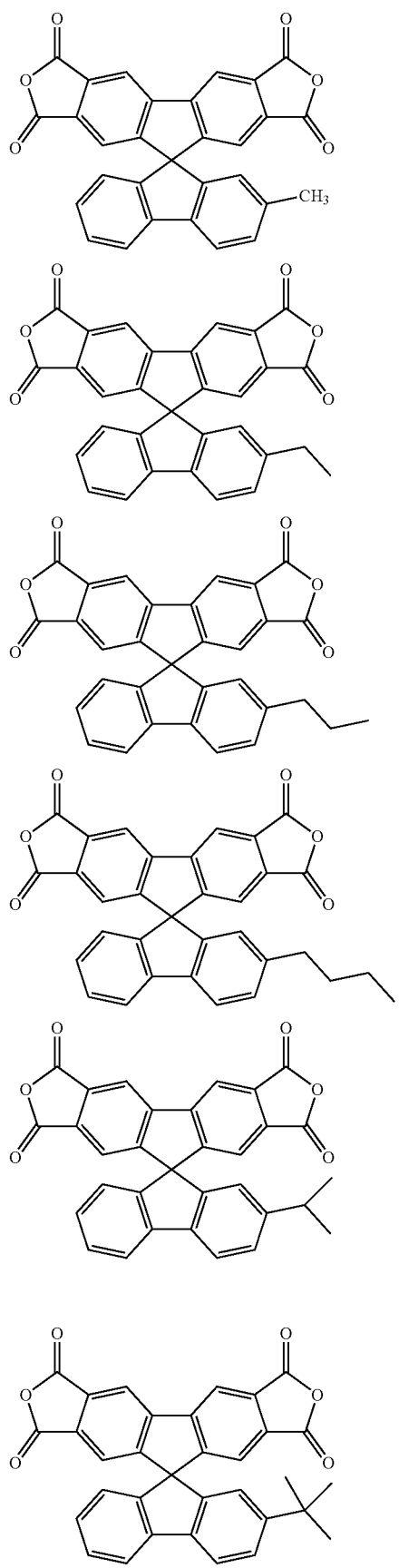
-continued
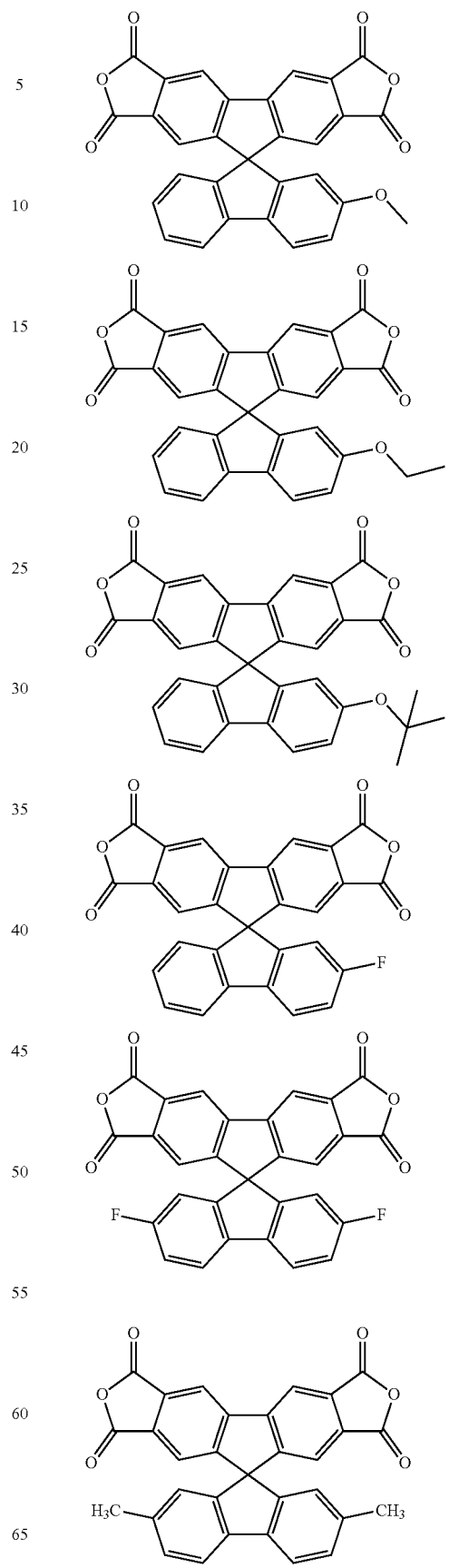

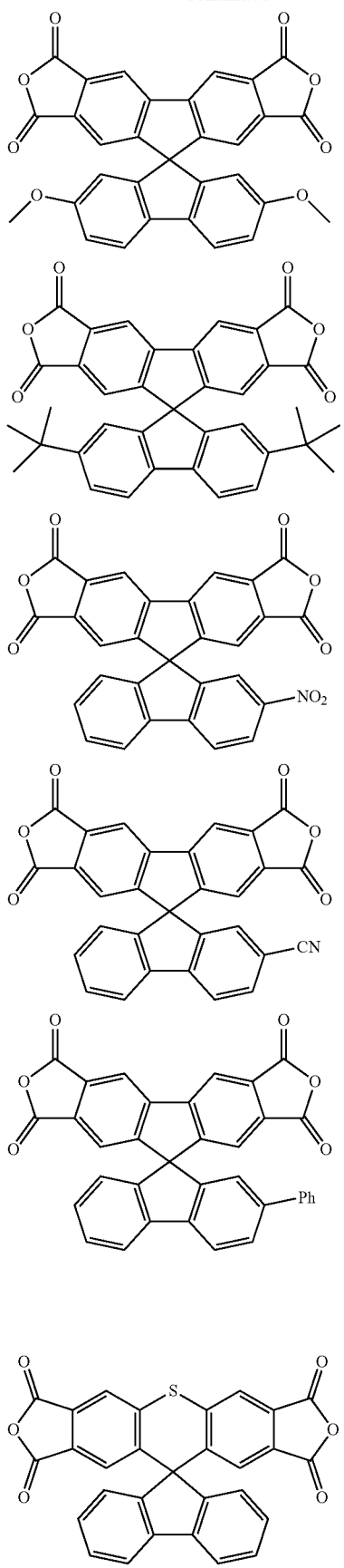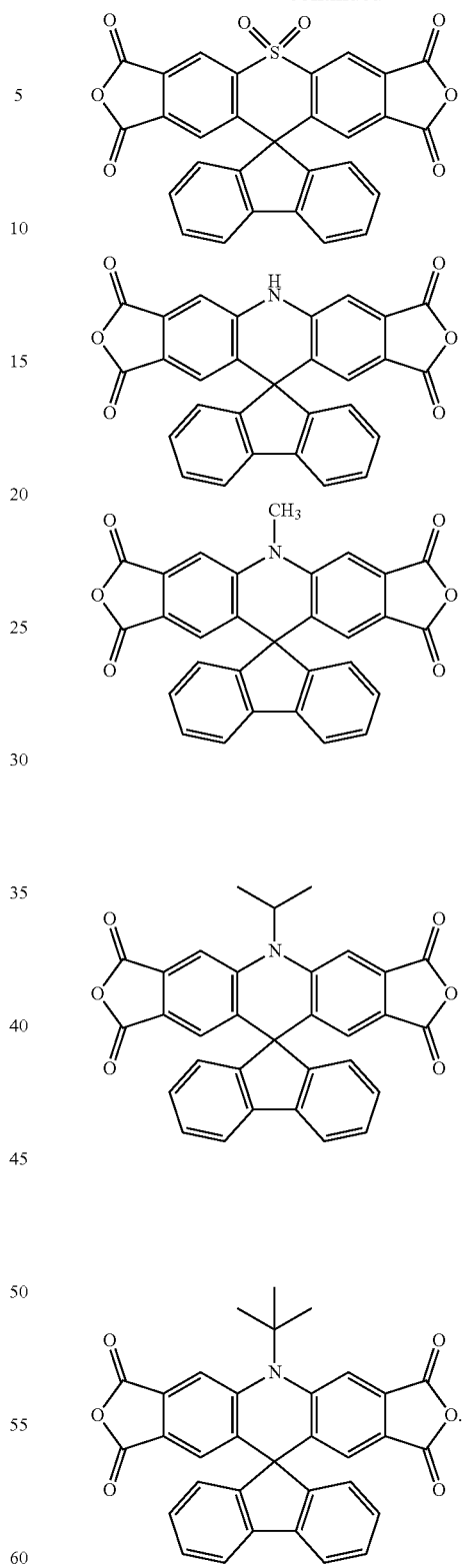
In another general aspect, a method for preparing the tetracarboxylic acid dianhydride represented by Chemical Formula 1 includes: specifically, dehydrating and cyclizing a compound represented by the following Chemical Formula A in the presence of a dehydrating agent:

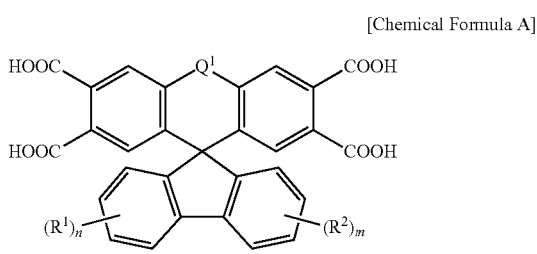

[Chemical Formula A]

wherein $Q^1$ is a single bond, —C(=O)—, —C(=O)O—, —C(=O)NH—, —S—, —SO$_2$—, —NR'—, —CH$_2$—, or a combination thereof, wherein R' is hydrogen or C1-C10 alkyl;

$R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent to form a ring; and n and m are independently of each other an integer selected from 0 to 4, and when n and m are an integer of 2 or more, $R^1$ and $R^2$ may be the same as or different from each other.

In the method for preparing the tetracarboxylic acid dianhydride represented by Chemical Formula 1, the dehydrating agent may be an acid anhydride.

In still another general aspect, a composition includes: the tetracarboxylic acid dianhydride represented by Chemical Formula 1.

The composition may further include an organic solvent.

The composition may include 1 to 30 wt % of the tetracarboxylic acid dianhydride represented by Chemical Formula 1.

Other features and aspects will be apparent from the following detailed description, the drawings, and the claims.

DETAILED DESCRIPTION OF EMBODIMENTS

In this specification, unless otherwise defined, all technical terms and scientific terms have the same meanings as those commonly understood by a person skilled in the art to which the present invention pertains. The terms used herein are only for effectively describing a certain specific example, and are not intended to limit the present invention.

The singular form used in the present specification may be intended to also include a plural form, unless otherwise indicated in the context.

In addition, units used in the present specification without particular mention is based on weights, and as an example, a unit of % or ratio refers to a wt % or a weight ratio, and the wt % refers to a wt % of any one component in a total composition occupied in the composition, unless otherwise defined.

In addition, the numerical range used in the present specification includes all values within the range including the lower limit and the upper limit, increments logically derived in a form and span in a defined range, all double limited values, and all possible combinations of the upper limit and the lower limit in the numerical range defined in different forms. Unless otherwise defined in the specification of the present invention, values which may be outside a numerical range due to experimental error or rounding of a value are also included in the defined numerical range.

The term "comprising" in the present specification may be an open-ended term implying further inclusion of other components, not exclusion of other components, unless otherwise stated.

The term "derived" in the present specification refers to at least any one of functional groups of a compound being modified, and specifically may include a modified form or released form of a functional group and/or a leaving group of a compound according to a reaction. In addition, when structures derived from compounds different from each other are the same, it may include a case in which a structure derived from any one compound has the same structure as that is derived from any other compound.

The term "polyimide precursor solution" in the present specification refers to a composition for preparing polyimide, and specifically, a polyimide precursor refers to a polymer including a structure unit having an amic acid moiety and may be equivalent to a polyamic acid. In addition, the polyimide precursor solution may be also used as a composition for preparing polyamideimide.

The term "polyimide film" in the present specification is a molded body of polyimide derived from a polyamide precursor solution and may be equivalent to polyimide.

The term "halogen" in the present specification refers to a fluorine (F), chlorine (Cl), bromine (Br), or iodine (I) atom.

The term "alkyl" in the present specification is an organic radical derived from an aliphatic hydrocarbon by removal of one hydrogen and may include both linear and branched forms.

The term "alkoxy" in the present specification is represented as *—O-alkyl, and the alkyl is as defined above.

The terms "haloalkyl" and "haloalkoxy" in the present specification refer to the alkyl or alkoxy having one hydrogen replaced by a halogen.

The term "aryl" in the present specification is an organic radical derived from an aromatic hydrocarbon by removal of one hydrogen, including a monocyclic or fused cyclic system, and even a form of plural aryls connected by a single bond.

The present inventors intensively studied polyimide having excellent thermal dimensional stability, and as a result, found that a more rigid linear structure is introduced to and also fluorene is included in a mother nucleus skeleton of a tetracarboxylic acid dianhydride, thereby not only satisfying significantly improved thermal dimensional stability but also increasing transparency. That is, the present inventors confirmed that polyimide derived from a tetracarboxylic acid dianhydride having the structural characteristics as such satisfies a low coefficient of linear thermal expansion, of course, and has excellent transparency and thermal resistance, thereby suggesting the present invention.

Hereinafter, an exemplary embodiment of the present invention will be described in more detail.

Specifically, the tetracarboxylic acid dianhydride according to an exemplary embodiment of the present invention may be represented by the following Chemical Formula 1:

[Chemical Formula 1]

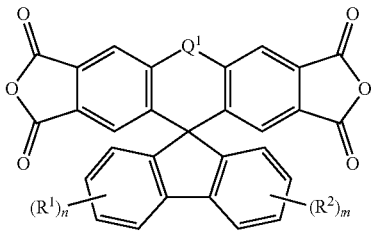

wherein

Q¹ is a single bond, —C(=O)—, —C(=O)O—, —C(=O)NH—, —NR'—, —S—, —SO₂—, —CH₂—, or a combination thereof, wherein R' is hydrogen or C1-C10 alkyl;

$R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent to form a ring; and n and m are independently of each other an integer selected from 0 to 4, and when n and m are an integer of 2 or more, $R^1$ and $R^2$ may be the same as or different from each other.

By satisfying the structure described above, the tetracarboxylic acid dianhydride according to an exemplary embodiment of the present invention may satisfy excellent thermal dimensional stability. That is, thermal resistance may be excellent. In addition, intermolecular packing density may be increased to provide a polyimide film having increased transparency and a decreased yellow index. However, when Q¹ is an oxygen atom in Chemical Formula 1, intramolecular bending occurs and polyimide derived therefrom has a decreased rigid structural characteristic. Thus, the polyimide including the structural characteristic as such (Q¹ is an oxygen atom) has low thermal dimensional stability.

The tetracarboxylic acid dianhydride according to an exemplary embodiment of the present invention may be selected from compounds represented by the following Chemical Formulae 2 to 5:

[Chemical Formula 2]

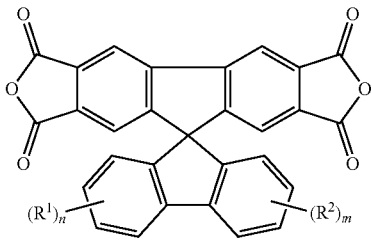

[Chemical Formula 3]

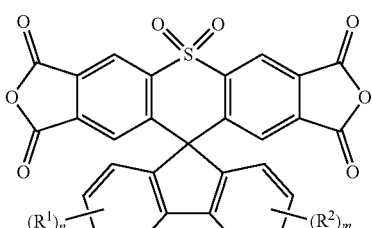

[Chemical Formula 4]

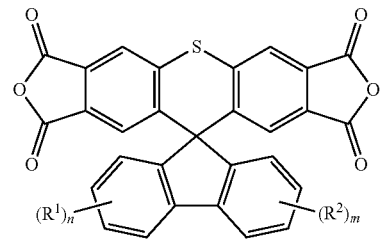

[Chemical Formula 5]

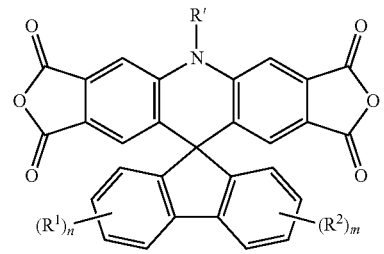

wherein $R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent to form a ring;

R' is hydrogen or C1-C4 alkyl; and n and m are independently of each other an integer selected from 0 to 4, and when n and m are an integer of 2 or more, $R^1$ and $R^2$ may be the same as or different from each other.

As an example, a tetracarboxylic acid dianhydride having a mother nucleus skeleton derived from spirobifluorene may have further improved thermal resistance and thus, also have excellent processability.

As an example, the compound represented by Chemical Formulae 3 to 5 has a further improved yellow index (YI) and a better total light transmittance at a 380 to 780 nm section, thereby providing a polyimide film having both a low coefficient of thermal expansion and high transparency.

In the tetracarboxylic acid dianhydride according to an exemplary embodiment of the present invention, in Chemical Formula 1, $R^1$ and $R^2$ may be independently of each other a halogen, hydroxy, thiol, nitro, cyano, C1-C10 alkyl, C1-C10 alkoxy, C6-C20 aryl, C1-C10 haloalkyl, or C1-C10 haloalkoxy, and n and m may be independently of each other an integer selected from 0 to 2.

As an example, in Chemical Formulae 2 to 5, $R^1$ and $R^2$ may be independently of each other a halogen, hydroxy, thiol, nitro, cyano, C1-C10 alkyl, C1-C10 alkoxy, C6-C20 aryl, C1-C10 haloalkyl, or C1-C10 haloalkoxy, and n and m may be independently of each other an integer selected from 0 to 2.

In the tetracarboxylic acid dianhydride according to an exemplary embodiment of the present invention, in Chemical Formula 1, $R^1$ and $R^2$ may be independently of each other a halogen, hydroxy, thiol, nitro, cyano, C1-C4 alkyl, C1-C4 alkoxy, C6-C18 aryl, C1-C4 haloalkyl, or C1-C4 haloalkoxy, and n and m may be independently of each other an integer selected from 0 to 2.

As an example, in Chemical Formulae 2 to 5, $R^1$ and $R^2$ may be independently of each other a halogen, hydroxy, thiol, nitro, cyano, C1-C4 alkyl, C1-C4 alkoxy, C6-C18 aryl, C1-C4 haloalkyl, or C1-C4 haloalkoxy, and n and m may be independently of each other an integer selected from 0 to 2.

In the tetracarboxylic acid dianhydride according to an exemplary embodiment of the present invention, in Chemical Formula 1, $R^1$ and $R^2$ may be independently of each other a halogen, nitro, cyano, C1-C4 alkyl, C1-C4 alkoxy, C6-C12 aryl, C1-C4 haloalkyl, or C1-C4 haloalkoxy, and n and m may be independently of each other an integer selected from 0 to 2 and satisfy 0 n+m 2.

As an example, in Chemical Formulae 2 to 5, $R^1$ and $R^2$ may be independently of each other a halogen, nitro, cyano, C1-C4 alkyl, C1-C4 alkoxy, C6-C12 aryl, C1-C4 haloalkyl, or C1-C4 haloalkoxy, and n and m may be independently of each other an integer selected from 0 to 2 and satisfy $0 \leq n+m \leq 2$.

As an example, in Chemical Formula 5, R' may be a hydrogen or C1-C4 alkyl.

As an example, one selected from $R^1$ and $R^2$ may be substituted at position 2 or 7 or at both positions of a fluorene ring. Specifically, one substituent selected from $R^1$ and $R^2$ may be substituted at an indicated position of the following Chemical Formula 1-1. In this case, it may be more effective in mechanical strength and flexibility.

[Chemical Formula 1-1]

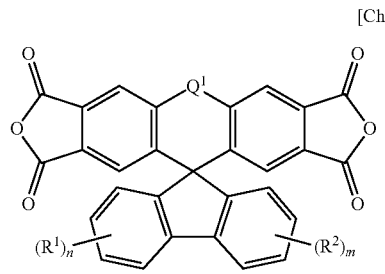

wherein $Q^1$ is a single bond, —NR'—, —S—, or —SO$_2$—, wherein R' is hydrogen or C1-C4 alkyl;

$R^1$ and $R^2$ are independently of each other a halogen, nitro, cyano, C1-C4 alkyl, C1-C4 alkoxy, C6-C12 aryl, C1-C4 haloalkyl, or C1-C4 haloalkoxy; and n and m are an integer selected from 0 to 2, and may satisfy $0 \leq n+m \leq 2$.

As an example, in Chemical Formula 1-1, $R^1$ or $R^2$ may be selected from a halogen selected from fluorine, chlorine, bromine, and iodine; alkyl selected from methyl, ethyl, propyl, and butyl; alkoxy selected from methoxy, ethoxy, propoxy, and butoxy; and aryl selected from phenyl and naphthyl.

The tetracarboxylic acid dianhydride according to an exemplary embodiment of the present invention may include at least one or two or more selected from the following structures, but is not limited thereto:

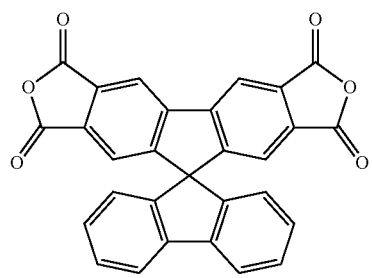

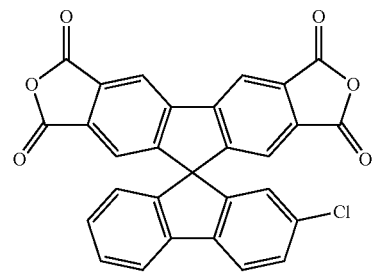

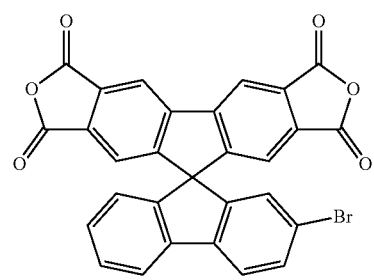

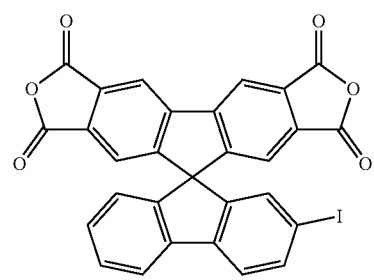

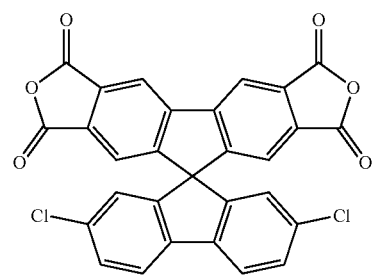

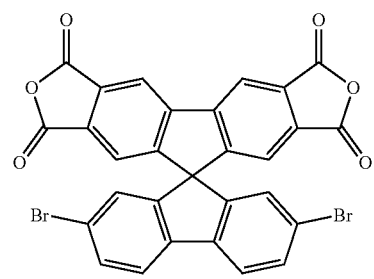

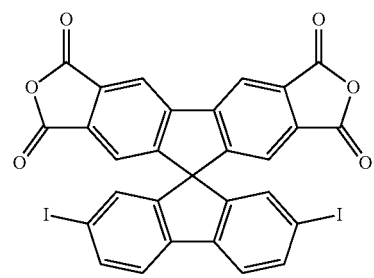

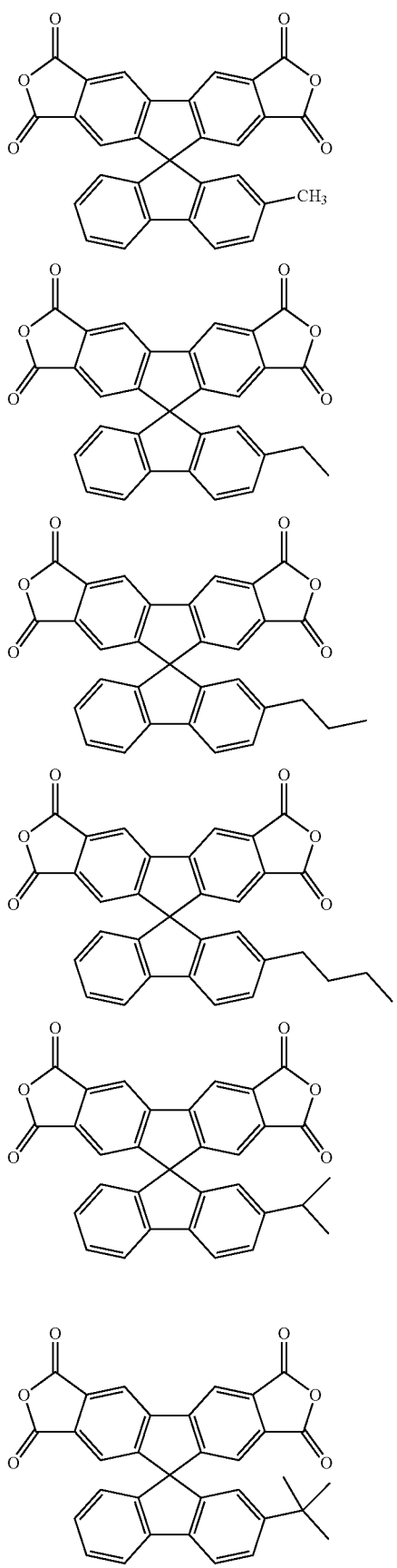
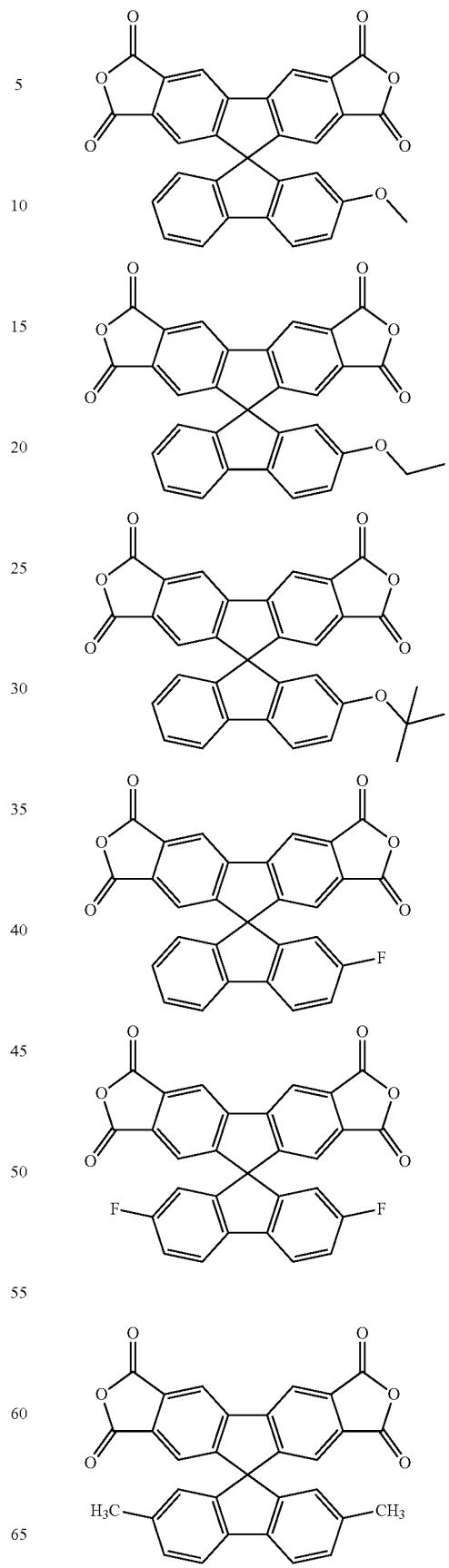

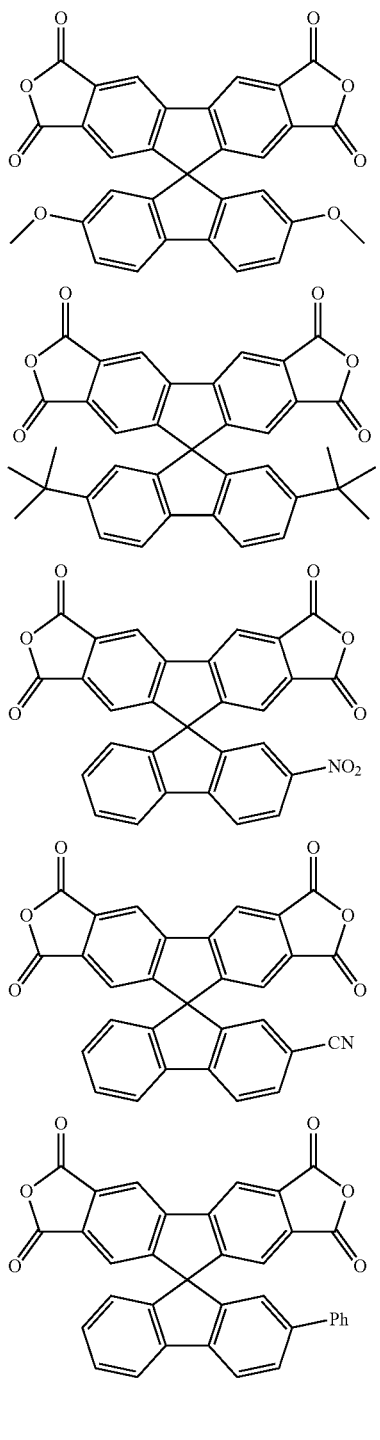
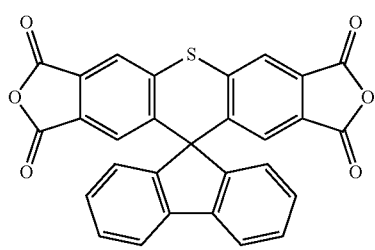
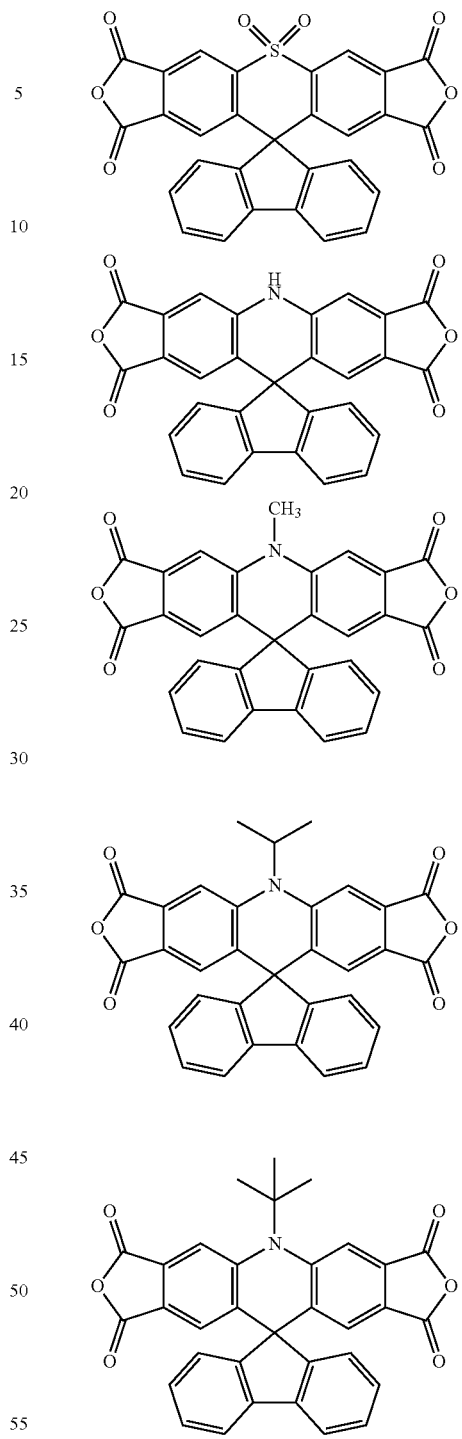

wherein Ph is phenyl.

In addition, another exemplary embodiment of the present invention may be a method for preparing the tetracarboxylic acid dianhydride.

Specifically, the method for preparing a tetracarboxylic acid dianhydride according to an exemplary embodiment of the present invention may include dehydrating and cyclizing a compound represented by the following Chemical Formula A in the presence of a dehydrating agent:

[Chemical Formula A]

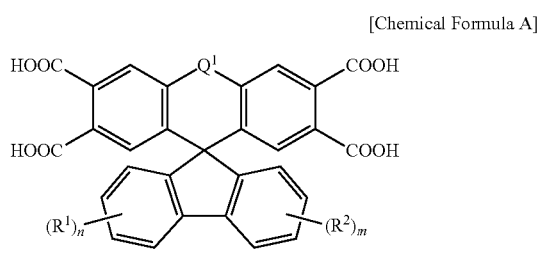

wherein $Q^1$ is a single bond, —C(=O)—, —C(=O)O—, —C(=O)NH—, —NR'—, —S—, —SO$_2$—, —CH$_2$—, or a combination thereof, wherein R' is hydrogen or C1-C10 alkyl;

$R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent to form a ring; and n and m are independently of each other an integer selected from 0 to 4, and when n and m are an integer of 2 or more, $R^1$ and $R^2$ may be the same as or different from each other.

As an example, the dehydrating agent may be an acid anhydride.

As an example, the acid anhydride may be selected from acetic anhydrides, phthalic anhydrides, maleic anhydrides, and the like, and specifically, may include acetic anhydrides.

As an example, the dehydrating agent may further include one or two or more selected from pyridine, isoquinoline, triethylamine, and the like.

As an example, the dehydrating agent may be introduced at 2 to 10 mol with respect to 1 mol of the compound represented by Chemical Formula A.

As an example, the step of dehydration and cyclization may be performed at 60 to 130° C. for 2 to 12 hours.

The method for preparing a tetracarboxylic acid dianhydride according to an exemplary embodiment of the present invention may be as shown in the following Reaction Formula 1, but may be variously modified by a common organic synthesis method, of course.

[Reaction Formula 1]

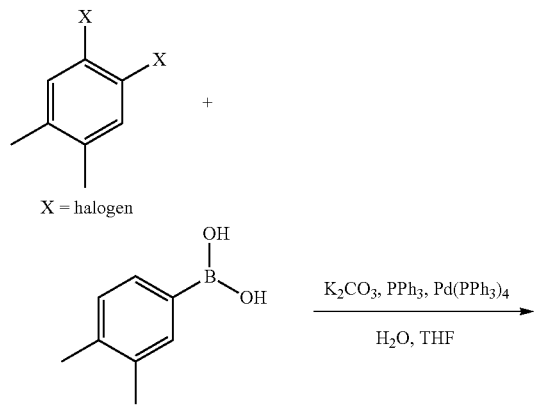

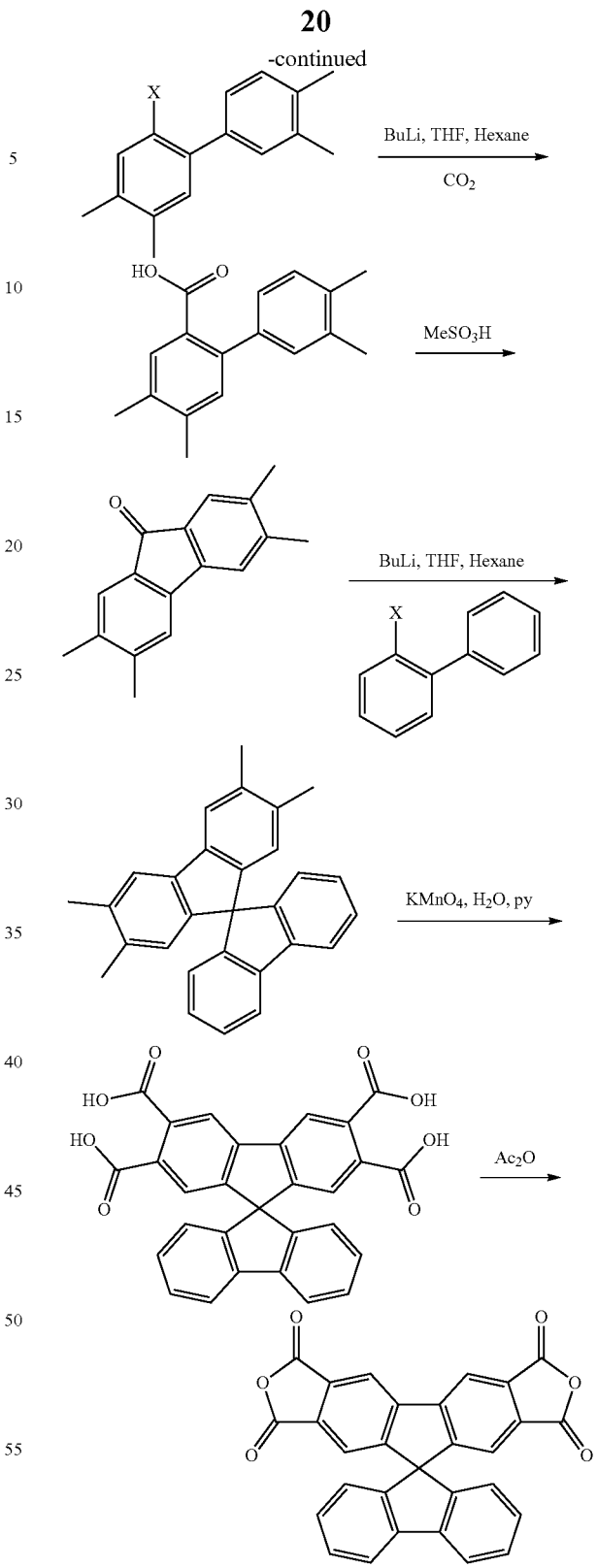

In addition, another exemplary embodiment of the present invention is a use of the tetracarboxylic acid dianhydride, and a specific embodiment thereof will be described later.

The first embodiment of the present invention may be a composition including the tetracarboxylic acid dianhydride represented by Chemical Formula 1.

A second embodiment of the present invention may be a polyimide precursor solution including a polyimide precursor derived from the tetracarboxylic acid dianhydride represented by Chemical Formula 1. Specifically, the polyimide precursor may be a polyamic acid obtained by a reaction of polymerization components including the tetracarboxylic acid dianhydride represented by Chemical Formula 1 and diamine.

A third embodiment of the present invention may be a polyamic acid which is a polyimide precursor solution including a polyimide precursor derived from the tetracarboxylic acid dianhydride represented by Chemical Formula 1 and further includes a tetracarboxylic acid dianhydride known in the art.

A fourth embodiment of the present invention may further include an organic solvent in the first to third embodiments described above.

Specifically, the composition or the solution of the first to fourth embodiments described above may be used for providing a polyimide film. In addition, the composition or the solution of the first to fourth embodiments described above may be used for preparing a polyamideimide film.

As described above, according to an exemplary embodiment of the present invention, a polyimide film which may implement high transparency and thermal resistance and has excellent thermal dimensional stability due to a substrate of which the stress is not increased even with a heat treatment at high temperature may be provided. In particular, according to an exemplary embodiment of the present invention, even in the case of including no tetracarboxylic acid dianhydride known in the art, a polyimide film having a low coefficient of linear thermal expansion may be provided. In addition, when the tetracarboxylic acid dianhydride known in the art is further included, a polyimide film having a further lowered coefficient of linear thermal expansion may be provided.

The composition or the polyimide precursor solution according to an exemplary embodiment of the present invention may be one or a mixture of two or more selected from ketones such as γ-butyrolactone, 1,3-dimethyl-2-imidazolidinone, methylethylketone, cyclohexanone, cyclopentanone, and 4-hydroxy-4-methyl-2-petanone; aromatic hydrocarbons such as toluene, xylene, and tetramethylbenzene; glycol ethers (cellosolve) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether, and triethylene glycol monoethyl ether; acetates such as ethyl acetate, butyl acetate, ethylene glycol monoethyl ether acetate, ethylene glycol monobutyl ether acetate, diethylene glycol monoethyl ether acetate, and dipropylene glycol monomethyl ether acetate; alcohols such as ethanol, propanol, ethylene glycol, propylene glycol, and carbitol; amides such as N,N-dimethylpropionamide (DMPA), N,N-diethylpropionamide (DEPA), N,N-dimethylacetamide (DMAc), N,N-diethylacetamide, N,N-dimethylformamide (DMF), N,N-diethylformamide (DEF), N-methylpyrrolidone (NMP), N-ethylpyrrolidone (NEP), and N,N-dimethylmethoxyacetamide, and the like.

As an example, the organic solvent may be one or a mixture of two or more selected from the amides.

As an example, the organic solvent may have a boiling point of 300° C. or lower. As an example, the organic solvent may be N,N-diethylformaide (DEF), N,N-diethylacetamide (DEAc), N-ethylpyrrolidone (NEP), N,N-dimethylpropionamide (DMPA), N,N-diethylpropionamide (DEPA), or a combination thereof.

The polyimide precursor solution according to an exemplary embodiment of the present invention may include aromatic diamine. Specifically, the aromatic diamine according to an exemplary embodiment of the present invention may include a unit represented by the following Chemical Formula 6:

[Chemical Formula 6]

wherein
$R^3$ is hydrogen, C1-C10 alkyl, or C1-C10 fluoroalkyl; and
p is an integer of 1 or 2.

As an example, the aromatic diamine may be aromatic diamine in a linear chain form and specifically, may be selected from compounds represented by the following Chemical Formulae 6-1 and 6-2. Here, the aromatic diamine may be used as one or a mixture of two or more, of course.

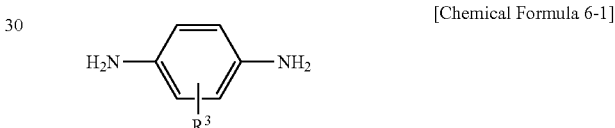

[Chemical Formula 6-1]

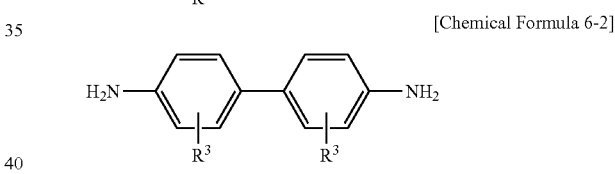

[Chemical Formula 6-2]

wherein
$R^3$ is independently of each other hydrogen, C1-C10 alkyl, or C1-C10 fluoroalkyl.

As an example, the aromatic diamine may be fluoro-based aromatic diamine including fluoroalkyl.

As an example, the aromatic diamine may be the compound represented by Chemical Formula 6-1 or 6-2, wherein $R^3$ is independently of each other C1-C7 fluoroalkyl.

As an example, the aromatic diamine may be the compound represented by Chemical Formula 6-1 or 6-2, wherein $R^3$ is independently of each other C1-C3 fluoroalkyl.

The polyimide precursor solution according to an exemplary embodiment of the present invention may include a tetracarboxylic acid dianhydride having a mother nucleus skeleton derived from spirobifluorene like the compound represented by Chemical Formula 2, in terms of imparting excellent processability with further improved thermal resistance.

The polyimide precursor solution according to an exemplary embodiment of the present invention may include one or more tetracarboxylic acid dianhydrides selected from the compounds represented by Chemical Formulae 3 to 5, in terms of implementing further improved yellow index (YI) and an excellent total light transmittance in a 380 to 780 nm section.

The polyimide precursor solution according to an exemplary embodiment of the present invention may include the tetracarboxylic acid dianhydride of Chemical Formula 1-1 wherein $R^1$ or $R^2$ is C1-C4 alkyl, in terms of implementing further improved mechanical strength and flexibility.

The polyimide precursor solution according to an exemplary embodiment of the present invention may further include a tetracarboxylic acid dianhydride known in the art selected from compounds represented by the following Chemical Formulae 7 and 8:

[Chemical Formula 7]

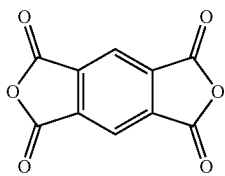

[Chemical Formula 8]

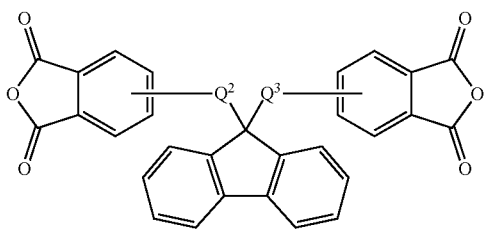

wherein $Q^2$ and $Q^3$ are a single bond, —O—, —C(=O)—, —C(=O)O—, —C(=O)NH—, —NR'—, —S—, —SO$_2$—, phenylene, or a combination thereof, wherein R' is hydrogen or C1-C10 alkyl.

The polyimide precursor solution according to an exemplary embodiment of the present invention may include the tetracarboxylic acid dianhydride represented by Chemical Formula 1 and diamine as polymerization components, as described above. Specifically, the polymerization component may include the tetracarboxylic acid dianhydride represented by Chemical Formula 1 in a range of 0.9 to 1.1 based on 1 mol of the diamine.

In addition, when the polyimide precursor solution according to an exemplary embodiment of the present invention further includes the tetracarboxylic acid dianhydride known in the art as described above, a mole ratio of a total content of the tetracarboxylic acid dianhydride represented by Chemical Formula 1 and the tetracarboxylic acid dianhydride known in the art to a content of the diamine may be 1:0.99 to 0.99:1, specifically 1:0.98 to 0.98:1.

In addition, when the polyimide precursor solution according to an exemplary embodiment of the present invention further includes the tetracarboxylic acid dianhydride known in the art as described above, the tetracarboxylic acid dianhydride represented by Chemical Formula 1 may be included at 10 to 99 mol %, based on the total content of the tetracarboxylic acid dianhydride represented by Chemical Formula 1 and the tetracarboxylic acid dianhydride known in the art. Otherwise, it may be included at 10 to 90 mol %, 20 to 50 mol %, or 20 to 30 mol %.

Specifically, the polyimide precursor solution according to an exemplary embodiment of the present invention may include a polyimide precursor including a repeating unit represented by the following Chemical Formula a which is a polymerization product of the polymerization components, that is, a polyamic acid:

[Chemical Formula a]

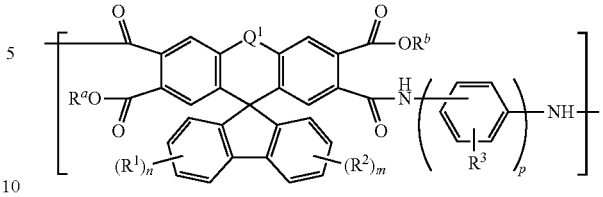

wherein $Q^1$ is a single bond, —C(=O)—, —C(=O)O—, —C(=O)NH—, —NR'—, —S—, —SO$_2$—, —CH$_2$—, or a combination thereof, wherein R' is hydrogen or C1-C10 alkyl;

$R^a$ and $R^b$ are independently of each other hydrogen or C1-C10 alkyl;

$R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent form a ring; and $R^3$ is hydrogen, C1-C10 alkyl, or C1-C10 fluoroalkyl;

p is an integer of 1 or 2; and n and m are independently of each other an integer selected from 0 to 4, and when n and m are an integer of 2 or more, $R^1$ and $R^2$ may be the same as or different from each other.

As an example, the polyimide precursor solution according to an exemplary embodiment of the present invention may have a solid content including the polyimide precursor including the repeating unit represented by Chemical Formula a of 10 to 40 wt %, 10 to 30 wt %, 10 to 20 wt %, or 10 to 13 wt %, based on the total weight. Here, the solid content may be the content of the polyamic acid and the residual amount may be the amount of the organic solvent.

As an example, the polyimide precursor solution according to an exemplary embodiment of the present invention may have a viscosity satisfying 2,000 to 10,000 cps. The viscosity may satisfy specifically 8,000 cps or less, more specifically 7,000 cps or less. When the viscosity range as such is satisfied, deformation efficiency when processing a polyimide film is better to provide an advantage in processing. Thus, a more uniform surface may be implemented. Here, the viscosity may refer to a value measured by piling up a sample at room temperature (25° C.) using a Brookfield RVDV-III viscometer spindle No. 52 and performing a stabilization operation for 2 minutes when a torque value is 80%.

The polyimide precursor solution according to an exemplary embodiment of the present invention may be obtained by polymerizing the polymerization components described above to prepare a polyamic acid including the repeating unit represented by Chemical Formula a and then performing imidization. As an example, the imidization may be performed by a chemical imidization method or a thermal imidization method.

The imidization according to the present invention may be performed by the thermal imidization method. By the method as such, uniform mechanical physical properties may be imparted to the entire film when imidized by heat at a high temperature. Specifically, the polyimide film according to the present invention may be prepared by a preparation method including applying and coating the polyimide precursor solution described above and then performing heat treatment.

As an example, the heat treatment may be performed at 500° C. or lower.

As an example, the heat treatment may include a first heat treatment step performed at 100° C. or lower; a second heat treatment step performed at higher than 100° C. and 300° C. or lower; and a third heat treatment step performed at higher than 300° C. and 500° C. or lower, but is not limited thereto.

As an example, the substrate may be a glass substrate, a metal substrate, or a plastic substrate, without particular limitation. Among them, the substrate may be the glass substrate which has excellent thermal and chemical stability during imidization and a curing process for the polyimide precursor solution and may be easily separated without damage to a polyimide film formed after curing.

As an example, a method for application and coating is not particularly limited, but for example, any one or more methods selected from a spin coating method, a dipping method, a spraying method, a die coating method, a bar coating method, a roll coating method, a meniscus method, a flexography method, a screen printing method, a bead coating method, an air knife coating method, a reverse roll coating method, a blade coating method, a casting coating method, a gravure coating method, and the like may be used.

As an example, after the heat treatment step, a drying step and a step of separation from the substrate may be further included.

As an example, a molecular weight of the polyamic acid including the repeating unit represented by Chemical Formula a is not particularly limited, but, an example, when the weight average molecular weight is in a range of 20,000 to 150,000 g/mol, better physical properties may be obtained.

In addition, the polyimide precursor solution according to an exemplary embodiment of the present invention may further include an additive such as a leveling agent, a flame retardant, an adhesion improver, inorganic particles, an antioxidant, a UV inhibitor, and a plasticizer.

Specifically, the polyimide film prepared from the polyimide precursor solution according to an exemplary embodiment, that is, polyimide may include a repeating unit represented by the following Chemical Formula b:

[Chemical Formula b]

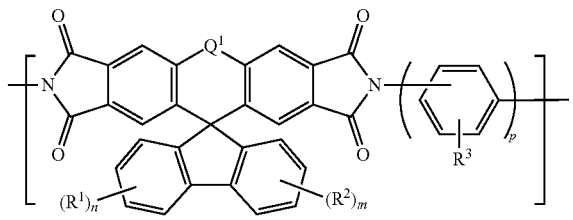

wherein $Q^1$ is a single bond, —C(=O)—, —C(=O)O—, —C(=O)NH—, —NR'—, —S—, —SO$_2$—, —CH$_2$—, or a combination thereof, wherein R' is hydrogen or C1-C10 alkyl;

$R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent to form a ring;

$R^3$ is hydrogen, C1-C10 alkyl, or C1-C10 fluoroalkyl;

p is an integer of 1 or 2; and n and m are independently of each other an integer selected from 0 to 4, and when n and m are an integer of 2 or more, $R^1$ and $R^2$ may be the same as or different from each other.

In addition, the polyimide film according to an exemplary embodiment of the present invention may further include a repeating unit represented by the following Chemical Formula c or d:

[Chemical Formula c]

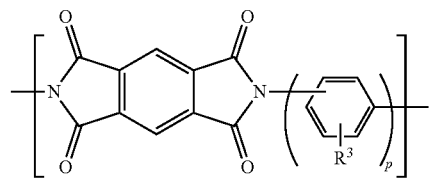

[Chemical Formula d]

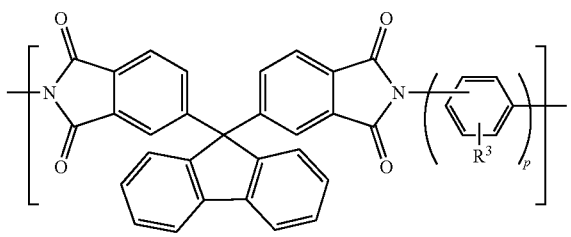

wherein $R^3$ is hydrogen, C1-C10 alkyl, or C1-C10 fluoroalkyl; and p is an integer of 1 or 2.

As described above, according to an exemplary embodiment of the present invention, as the repeating unit derived from the tetracarboxylic acid dianhydride represented by Chemical Formula 1 is included, a polyimide film having optical properties, thermal resistance, mechanical strength, and flexibility which are all excellent may be provided. Thus, the polyimide film may be used in various fields such as an element substrate, a display cover substrate, an optical film, an integrated circuit (IC) package, an electrodeposition film, a multilayer flexible printed circuit (FRC), a tape, a touch panel, and an optical disc protective film.

The polyimide film according to an exemplary embodiment of the present invention, that is, polyimide may have a weight average molecular weight of 10,000 to 200,000 g/mol, 20,000 to 100,000 g/mol, or 30,000 to 100,000 g/mol. In addition, the polyimide according to the present invention may have a molecular weight distribution (Mw/Mn) satisfying a range of 1.1 to 2.5. When the weight average molecular weight and the molecular weight distribution of the polyimide are satisfied, it is advantageous for the characteristics of the polyimide film such as optical properties, thermal resistance, mechanical strength, and flexibility.

The polyimide film according to an exemplary embodiment of the present invention may have a thickness of 5 to 15 μm.

The polyimide film according to an exemplary embodiment of the present invention may have excellent thermal resistance properties depending on a temperature change. Specifically, as a result of measuring a thermal expansion change pattern when subjected to a primary heating process at a heating rate of 5° C./min in a temperature range of 100° C. to 450° C. in the thickness range described above and then cooled at a cooling rate of 4° C./min in a temperature range of 400° C. to 100° C. using TMA (Q400 available from TA), the polyimide film may satisfy 50 ppm/° C. or less. Specifically, the polyimide film may satisfy the coefficient of thermal expansion (CTE) of 45 ppm/° C. or less, more specifically in a range of −15 to 45 ppm/° C.

The polyimide film according to an exemplary embodiment of the present invention may satisfy a haze in accordance with ASTM D1003 in a range of 2 or less, specifically 1 or less, more specifically 0.5 or less, and most specifically 0.01 to 0.3, in the thickness range described above. Since the haze value as such is satisfied, a polyimide film having improved transparency may be provided.

In addition, the polyimide film according to an exemplary embodiment of the present invention has an excellent light transmittance and an excellent yellow index, thereby representing significantly improved transparency and optical properties. Specifically, the polyimide film may have YI in accordance with ASTM E313 of 15 or less and a total light transmittance in a 380 to 780 nm section in accordance with ASTM D1746 of 80% or more, more specifically YI of 13 or less and a total light transmittance of 85% or more, and most specifically YI of 11 or less and a total light transmittance of 87% to 99%.

The polyimide film according to an exemplary embodiment of the present invention may have a modulus in accordance with ASTM D882 of 5.0 or more and an elongation of 15% or more, in the thickness range described above. Specifically, the polyimide film may have a modulus of 5.5 or more and an elongation of 15% or more, and more specifically a modulus of 6.0 or more and an elongation of 15% or more. When these characteristics are satisfied, the polyimide film may have excellent rigidity and secure further sufficient flexibility, thereby having a flexible property from external impact.

The polyimide film according to an exemplary embodiment of the present invention may satisfy all of the physical properties described above at the same time, but the present invention is not limited thereto.

The polyimide film according to an exemplary embodiment of the present invention may satisfy excellent optical properties, thermal resistance, mechanical strength, and flexibility at the same time by a rigid structure derived from the tetracarboxylic acid dianhydride represented by Chemical Formula 1. In particular, since the polyimide film may represent excellent thermal resistance to thermal shrinkage behavior which may occur in a process at a high temperature and also may represent excellent colorless transparent optical properties, the polyimide film may be used in various fields such as an element substrate, a display substrate, an optical film, an integrated circuit (IC) package, an electrode-position film (adhesive film), a multilayer flexible printed circuit (FRC), a tape, a touch panel, and an optical disc protective film.

The polyimide film according to an exemplary embodiment of the present invention may be used in the form of being included as two or more layers.

In addition, another exemplary embodiment of the present invention may be a photoelectric device and a flexible display including the polyimide film or a multilayer structure in the form in which the polyimide films are included as a flexible substrate.

As an example, the photoelectric device may be an optical component, a switch, an optical modulator, and also, is appropriate as a high thermal resistant substrate material requiring a micropattern formation characteristic.

As an example, the flexible display may be appropriate for a liquid crystal display device (LCD), an organic light emitting diode (OLED), and the like, and particularly, may be appropriate for an OLED device using a low temperature polysilicon (LTPS) process requiring a process at a high temperature, but is not limited thereto.

Hereinafter, the present invention will be described by the specific Examples and Comparative Examples of the present invention. The following Examples are for describing the technical idea of the present invention, and it is apparent to a person skilled in the art that the present invention is not limited thereto.

(Evaluation Method)

1. Coefficient of Linear Thermal Expansion (CTE) and Glass Transition Temperature (Tg)

The coefficient of linear thermal expansion was measured in accordance with a TMA-method using TMA (available from TA Instrument, Discovery 450). A specimen size was 5 mm×20 mm, a loading was 0.02 N, and a heating rate was 5° C./min. The CTE value was measured in a heating section at a temperature in a range of 100° C. to 450° C.

The Tg value was measured as a TMA graph inflection point in a heating section of 100° C. to 450° C.

2. Haze

The haze was measured using a spectrophotometer (available from Nippon Denshoku, COH-400), on a polyimide film having a thickness of 50 μm, in accordance with the standard of ASTM D1003. The unit was %.

3. Yellow Index (YI)

The yellow index was measured using a colorimeter (available from HunterLab, ColorQuest XE), on a polyimide film having a thickness of 10 μm, in accordance with the standard of ASTM E313.

4. Total Light Transmittance

The total light transmittance was measured in the entire wavelength range of 380 to 780 nm using a spectrophotometer (available from SHIMADZU, MPC-3100) on a polyimide film having a thickness of 10 μm, in accordance with the standard of ASTM D1746. The unit was %.

5. Modulus and Elongation

In accordance with ASTM D882, the elongation was measured using UTM 3365 available from Instron, under the condition of pulling a polyimide film having a thickness of 10 μm, a length of 40 mm and a width of 5 mm at 10 mm/min at 25° C. The unit of the modulus was GPa and the unit of the elongation was %.

6. Thickness

PAA was coated on a 0.5T glass and cured to obtain a substrate, and the thickness of the substrate was measured using a film thickness measuring instrument (Alpha step D500). The unit was μm.

7. Viscosity

The viscosity may refer to a value measured by piling up a sample at room temperature (25° C.) using a Brookfield RVDV-III viscometer spindle No. 52, allowing the sample to stand for 2 minutes when a torque value is 80%, and then stabilizing the sample. The unit was cps.

8. C.R. Test (Chemical Resistance Test)

Polyimide film curing conditions: Multi-step (80° C./30 min, 220° C./30 min, and 450° C./60 min)

Evaluation was as follows: ○: no film deformation, Δ: occurrence of partial film deformation, x: occurrence of film deformation.

9. Weight Average Molecular Weight

Measurement was performed by dissolving a film in a DMAc eluent containing 0.05 M LiBr. For GPC, Waters GPC system, Waters 1515 isocratic HPLC Pump, and Waters 2414 Reflective Index detector were used, for a column, Olexis, Polypore and a mixed D column were connected and polymethylmethacrylate (PMMA STD) was used as a standard material, and analysis was performed at 35° C. at a flow rate of 1 mL/min.

Example 1

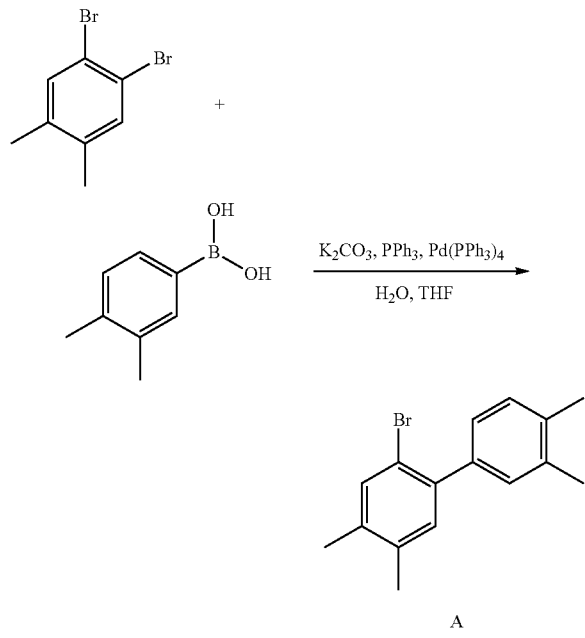

Step 1. Material A 3,4-Dimethylphenylboronic acid (7.95 g, 53.0 mmol), 1,2-dibromo-4,5-dimethylbenzene (14 g, 53.0 mmol), triphenylphosphine (0.42 g, 1.59 mmol), and K$_2$CO$_3$ (21.9 g, 159 mmol) were added to a mixed solution of 100 ml of degassed water and 70 ml of tetrahydrofuran (THF) in a nitrogen environment. The temperature was raised to 80° C., Pd(PPh$_3$)$_4$ (0.61 g, 0.53 mmol) was added, and stirring was performed for 30 hours. The temperature was lowered to room temperature, the organic solvent was removed by distillation under reduced pressure, 100 ml of dichloromethane (DCM) and 50 ml of water were added, an organic layer was washed with water, and moisture was removed using anhydrous MgSO$_4$. After MgSO$_4$ filtering, the solvent was removed and the material was separated with column chromatography to obtain Material A with a yield of 75%.

HRMS (EI, m/z): [M+] calculated for C16H13Br, 288.05; found, 269.16.

$^1$H-NMR (ppm, CDCl$_3$): 7.44 (1H, s), 7.15-7.20 (3H, m), 7.10 (1H, s), 2.33 (6H, s), 2.29 (3H, s), 2.25 (3H, s).

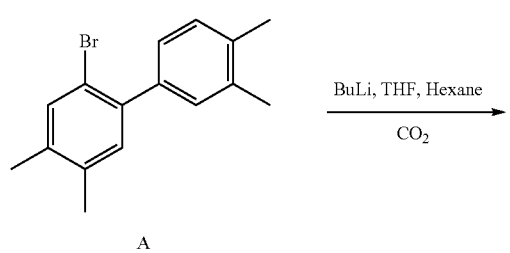

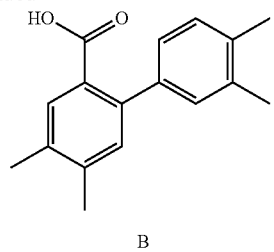

Step 2. Material B

Material A (5.65 g, 19.5 mmol) was dissolved in 80 ml of anhydrous tetrahydrofuran (THF) in a nitrogen environment and n-butyl lithium (9.37 ml of a solution 2.5 M in hexane, 23.4 mmol) was slowly added at −78° C. for 1 hour. Anhydrous CO$_2$ was blown in the solution for 4 hours, 60 ml of water was added to terminate the reaction, and the organic solvent was removed by distillation under reduced pressure. 100 ml of water and 50 ml of DCM were added, an aqueous layer was washed with DCM, a 0.1 N HCl solution was added to the aqueous layer to bring pH to 4, and then a precipitated organic material was extracted with ether. Anhydrous MgSO$_4$ was used to remove moisture and filtered, the solvent was removed, and the material was separated with column chromatography to obtain Material B with a yield of 65%.

HRMS (EI, m/z): [M+] calculated for C17H18O2, 254.13; found, 255.32.

$^1$H-NMR (ppm, CDCl$_3$): 7.75 (1H, s), 7.12-7.15 (3H, m), 7.07 (1H, s), 2.34 (s, 6H), 2.31 (6H, s).

Step 3. Material C

Material B (4.73 g, 18.6 mmol) was dissolved in 50 g of MeSO$_3$H in a nitrogen environment and stirring was performed at 50° C. for 18 hours. The reactant was poured into 500 ml of water at 0° C., a produced solid was filtered, and recrystallization was performed using methanol (MeOH) to obtain Material C with a yield of 85%.

HRMS (EI, m/z): [M+] calculated for C17H16O, 236.12; found, 237.25.

$^1$H-NMR (ppm, CDCl$_3$): 7.24 (2H, s), 2.33 (6H, s), 2.28 (6H, s).

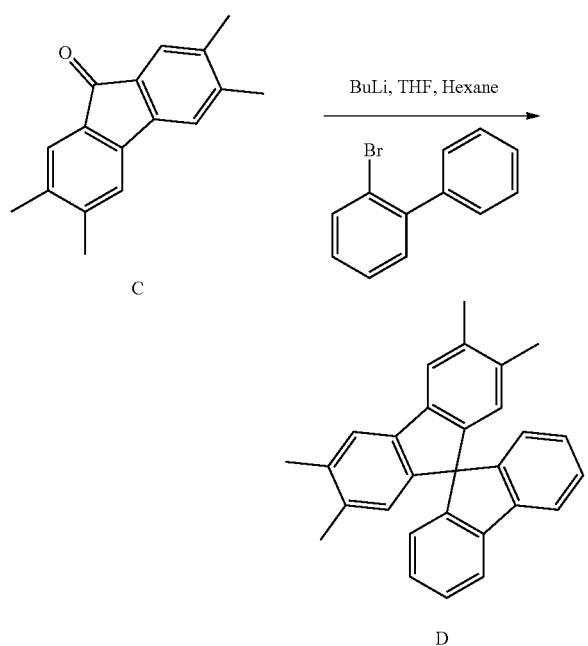 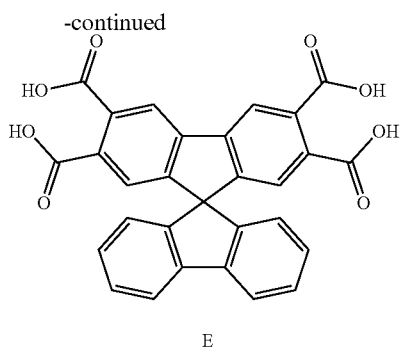

Step 4. Material D

2-Bromo-1,1'-biphenyl (4.0 g, 17.16 mmol) was dissolved 80 ml of anhydrous tetrahydrofuran (THF) in a nitrogen environment and n-butyl lithium (7.5 ml of a solution 2.5 M in hexane, 18.7 mmol) was slowly added at −78° C. for 10 minutes. After stirring for 1 hour, Material C (3.69 g, 15.6 mmol) was added to a reactant and stirring was performed for 12 hours while raising a temperature to room temperature. 80 ml of water was added, pressure was reduced to remove a solvent, and 100 ml of dichloromethane (DCM) was added to extract an organic material. Anhydrous MgSO$_4$ was used to remove moisture and filtered to remove the solvent, and then the material was added to 50 ml of acetic acid at 0° C. 1 ml of 35 wt % HCl was added, heating to reflux was performed for 4 hours, and then stirring was performed at room temperature for 1 hour. The reactant was poured into 200 ml of ice water, a produced solid was filtered, and methanol (MeOH) was used to perform precipitation and stirring, thereby obtaining Material D with a yield of 87%.

HRMS (EI, m/z): [M+] calculated for C29H24, 372.19; found, 373.05.

$^1$H-NMR (ppm, CDCl$_3$): 7.84-7.91 (4H, m), 7.59 (2H, s), 6.73-6.80 (4H, m), 6.49 (2H, s), 2.35 (6H, s), 2.11 (6H, s).

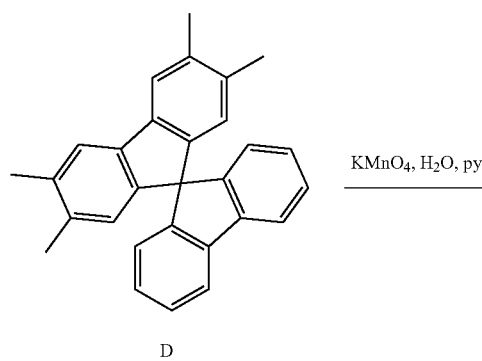

Step 5. Material E

Material D (3.95 g, 10.6 mmol) was dissolved in a mixed solvent of 50 ml of pyridine (Py) and 50 ml of water, and KMnO$_4$ (33.5 g, 212 mmol) dissolved in 100 ml of water was slowly added for 4 hours. After heating to reflux for 6 hours, filtration was performed to remove a solid material, and the temperature was lowered to room temperature to remove a solvent. A 0.1 N HCl solution was added to an aqueous layer to bring pH to 4 and a precipitated solid material was filtered and dried to obtain Material E with a yield of 80%.

HRMS (EI, m/z): [M+] calculated for C29H16O8, 492.08; found, 493.00.

$^1$H-NMR (ppm, D20): 7.97 (8H, s), 7.91 (4H, s).

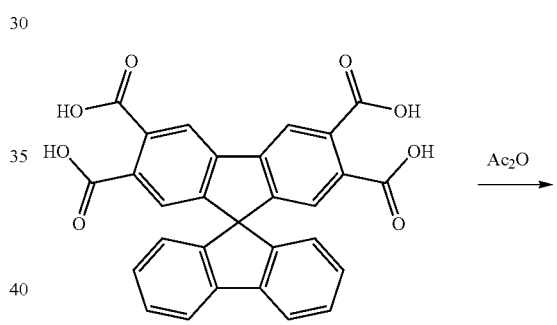 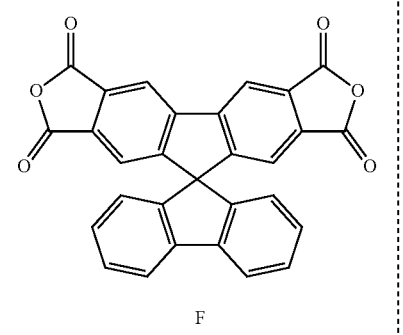

Step 6. Material F

Material E (3.80 g, 7.72 mmol) was dissolved in acetic acid anhydride (100 ml) in a nitrogen environment, heating to reflux was performed for 6 hours, and then the temperature was lowered to room temperature. The produced solid was filtered and washed using acetic acid anhydride, and then Material F was obtained with a yield of 90%.

HRMS (EI, m/z) [M+] calculated for C29H12O6, 456.06; found, 457.11.

Example 2

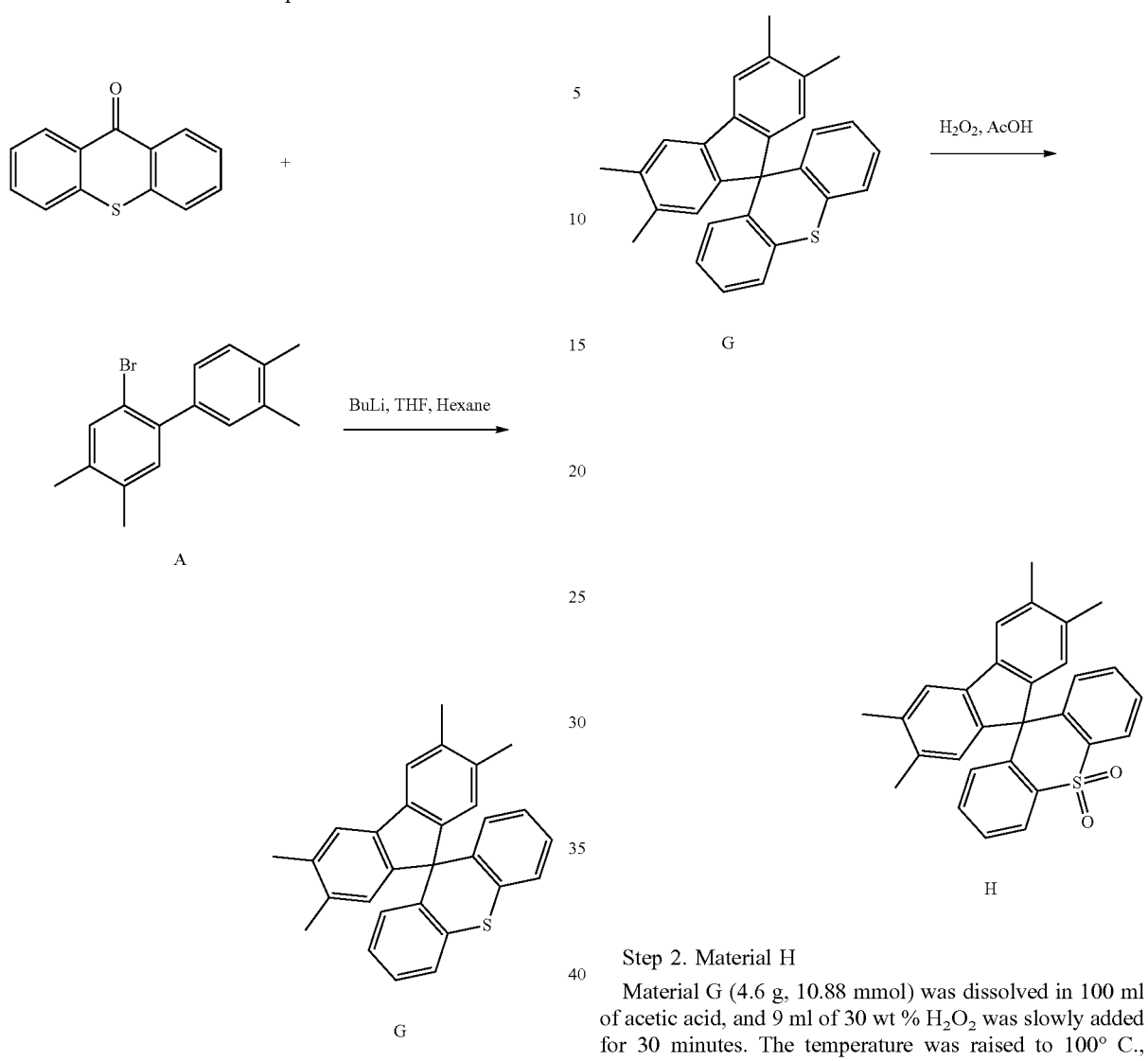

Step 1. Material G

Material A (5.0 g, 17.47 mmol) was dissolved in 100 ml of anhydrous tetrahydrofuran (THF), the temperature was lowered to −78° C., and then n-butyl lithium (7.6 ml of a solution 2.5 M in hexane, 18.8 mmol) was slowly added for 10 minutes. After stirring for 1 hour, 9H-thioxanthen-9-one (3.375 g, 15.9 mmol) was added to a reactant, and stirring was performed for 12 hours while the temperature was raised to room temperature. 100 ml of water was added, pressure was reduced to remove a solvent, and 100 ml of dichloromethane (DCM) was added to extract an organic material. Anhydrous $MgSO_4$ was used to remove moisture and filtered to remove the solvent, and then the material was added to 50 ml of acetic acid at 0° C. 1 ml of 35 wt % HCl was added, heating to reflux was performed for 4 hours, and then stirring was performed at room temperature for 1 hour. The reactant was poured into 200 ml of water, a produced solid was filtered, and MeOH was used to perform precipitation and stirring, thereby obtaining Material G with a yield of 88%.

HRMS (EI, m/z): [M+] calculated for C29H24S, 404.16; found, 405.15.

Step 2. Material H

Material G (4.6 g, 10.88 mmol) was dissolved in 100 ml of acetic acid, and 9 ml of 30 wt % $H_2O_2$ was slowly added for 30 minutes. The temperature was raised to 100° C., stirring was performed for 8 hours, and the temperature was lowered to room temperature. The produced solid material was filtered, was further washed with 20 ml acetic acid and 20 ml of heptane, and was dried, thereby obtaining Material H with a yield of 89%.

HRMS (EI, m/z): [M+] calculated for C29H24S, 404.16; found, 405.15.

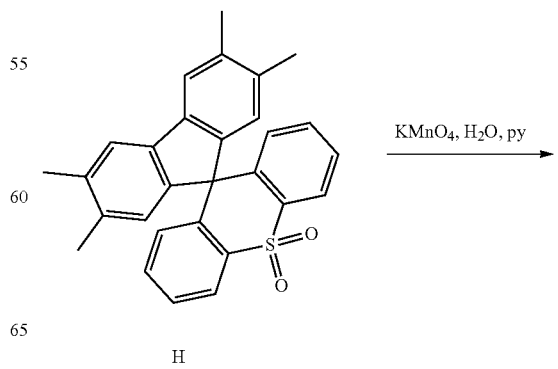

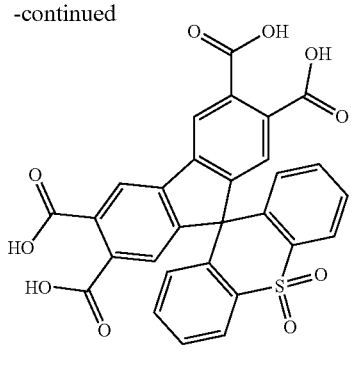

I

Step 3. Material I

Material H (4.0 g, 9.89 mmol) was dissolved in a mixed solvent of 50 ml of pyridine (Py) and 50 ml of water, and KMnO$_4$ (31.6 g, 200 mmol) dissolved in 100 ml of water was slowly added for 4 hours. After heating to reflux for 6 hours, filtration was performed to remove a solid material, and the temperature was lowered to room temperature to remove a solvent. A 0.1 N HCl solution was added to an aqueous layer to bring pH to 4 and a precipitated solid material was filtered and dried to obtain Material I with a yield of 85%.

HRMS (EI, m/z) [M+] calculated for C29H16O10S, 556.05; found, 557.04.

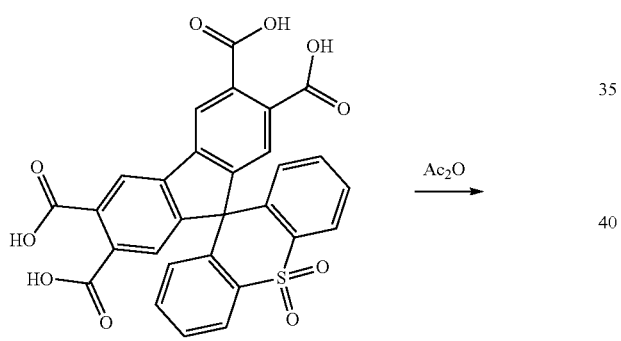

Step 4. Material J

Material I (3.6 g, 6.47 mmol) was dissolved in acetic acid anhydride (80 ml) in a nitrogen environment, heating to reflux was performed for 6 hours, and then the temperature was lowered to room temperature. The produced solid was filtered, washed using acetic acid anhydride, and dried to obtain Material J with a yield of 90%.

HRMS (EI, m/z): [M+] calculated for C29H12O6, 556.05; found, 557.03.

Example 3

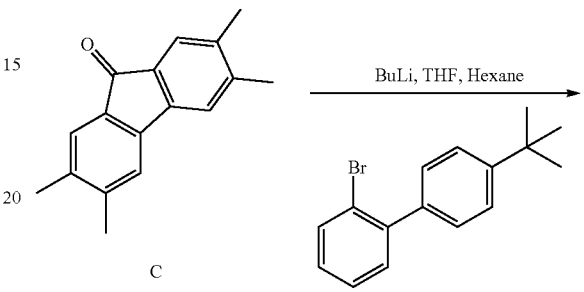

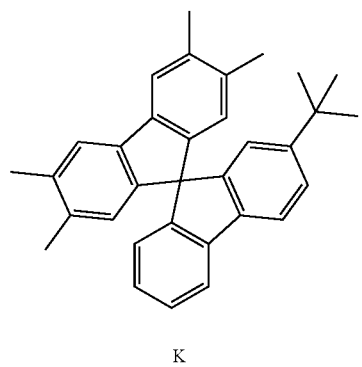

K

Step 1. Material K

2-Bromo-4'-tert-butyl-1,1'-biphenyl (5.0 g, 17.29 mmol) was 80 ml of anhydrous tetrahydrofuran (THF) in a nitrogen environment, the temperature was lowered to −78° C., and then n-butyl lithium (7.6 ml of a solution 2.5 M in hexane, 18.8 mmol) was slowly added for 10 minutes. After stirring for 1 hour, Material C (3.73 g, 15.8 mmol) was added to a reactant and stirring was performed for 12 hours while raising a temperature to room temperature. 80 ml of water was added, pressure was reduced to remove a solvent, and 100 ml of dichloromethane (DCM) was added to extract an organic material. Anhydrous MgSO$_4$ was used to remove moisture and filtered to remove the solvent, and then the material was added to 50 ml of acetic acid at 0° C. 1 ml of 35 wt % HCl was added, heating to reflux was performed for 4 hours, and then stirring was performed at room temperature for 1 hour. The reactant was poured into 200 ml of water at 0° C., a produced solid was filtered, and methanol (MeOH) was used to perform precipitation and stirring, thereby obtaining Material K with a yield of 85%.

HRMS (EI, m/z): [M+] calculated for C33H32, 428.25; found, 428.20.

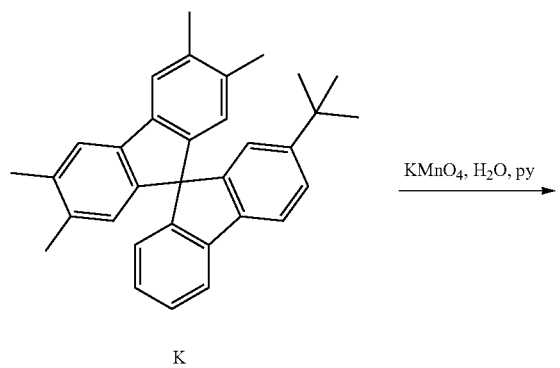

K

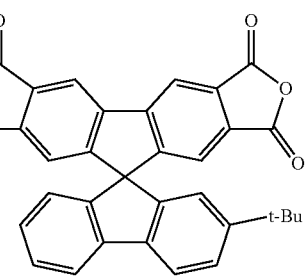

M

Step 3. Material M

Material L (3.00 g, 5.47 mmol) was dissolved in acetic anhydride (80 ml) in a nitrogen environment, heating to reflux was performed for 6 hours, and then the temperature was lowered to room temperature. The produced solid was filtered and washed using acetic acid anhydride, and then Material M was obtained with a yield of 90%.

HRMS (EI, m/z): [M+] calculated for C33H20O6, 512.13; found, 513.12.

Preparation Example 1

TFMB (0.999)/Example 1 (1.0), unit: mole ratio

A container with a stirrer in which a nitrogen stream flows was filled with 176 g of N,N-dimethylpropionamide (DMPA), and then 14.03 g of 2,2'-bis(trifluoromethyl)-4,4'-biphenyl diamine (TFMB) was dissolved in the state in which the temperature of the reactor was maintained at 25° C. 20 g of a novel monomer 1 (Example 1, Material F) was added thereto at the same temperature and stirring was performed for a certain period of time while dissolving the monomer. Thereafter, DMPA was added so that a solid concentration was 13 wt %, thereby preparing a polyimide precursor solution 1. The polyimide precursor solution 1 had a viscosity of 4,500 cp.

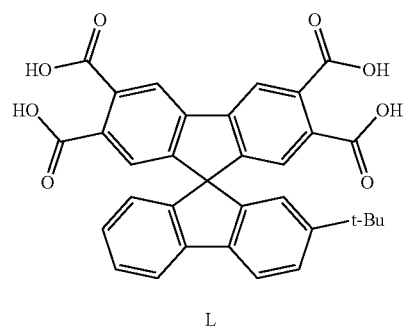

L

Step 2. Material L

Material K (3.95 g, 9.22 mmol) was dissolved in a mixed solvent of 50 ml of pyridine (Py) and 50 ml of water, and KMnO₄ (31.0 g, 190 mmol) dissolved in 100 ml of water was slowly added for 4 hours. After heating to reflux for 6 hours, filtration was performed to remove a solid material, and the temperature was lowered to room temperature to remove a solvent. A 0.1 N HCl solution was added to an aqueous layer to bring pH to 4 and a precipitated solid material was filtered and dried to obtain Material L with a yield of 81%.

HRMS (EI, m/z): [M+] calculated for C33H24O8, 548.15; found, 548.12.

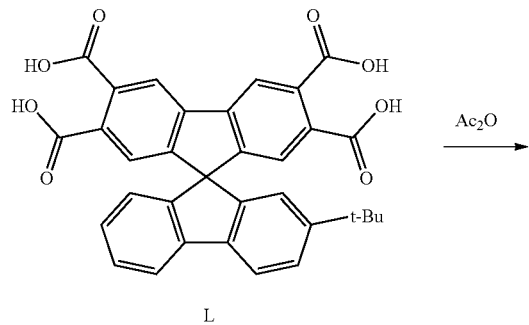

L

Preparation Example 2

TFMB (0.999)/Example 1 (0.2)/PMDA (0.8), unit: mole ratio

A container with a stirrer in which a nitrogen stream flows was filled with 175 g of N,N-dimethylpropionamide (DMPA), and then 18.33 g of 2,2'-bis(trifluoromethyl)-4,4'-biphenyl diamine (TFMB) was dissolved in the state in which the temperature of the reactor was maintained at 25° C. 5.22 g of a novel monomer 1 (Example 1, Material F) and 10 g of pyromellitic dianhydride (PMDA) were added thereto at the same temperature and stirring was performed for a certain period of time while dissolving the monomer. Thereafter, DMPA was added so that the solid concentration of the polyimide precursor solution was 13 wt %, thereby preparing a polyimide precursor solution 2. The polyimide precursor solution 2 had a viscosity of 5,200 cp.

Preparation Example 3

TFMB (0.999)/Example 2 (1.0), unit: mole ratio

A container with a stirrer in which a nitrogen stream flows was filled with 169 g of N,N-dimethylpropionamide (DMPA), and then 12.29 g of 2,2'-bis(trifluoromethyl)-4,4'-biphenyl diamine (TFMB) was dissolved in the state in which the temperature of the reactor was maintained at 25° C. 20 g of a novel monomer 2 (Example 2, Material J) was added thereto at the same temperature and stirring was performed for a certain period of time while dissolving the monomer. Thereafter, DMPA was added so that a solid concentration was 13 wt %, thereby preparing a polyimide precursor solution 3. The polyimide precursor solution 3 had a viscosity of 4,200 cp.

Preparation Example 4

TFMB (0.999)/Example 3 (1.0), unit: mole ratio
A container with a stirrer in which a nitrogen stream flows was filled with 170 g of N,N-dimethylpropionamide (DMPA), and then 12.48 g of 2,2'-bis(trifluoromethyl)-4,4'-biphenyl diamine (TFMB) was dissolved in the state in which the temperature of the reactor was maintained at 25° C. 20 g of a novel monomer 3 (Example 3, Material M) was added thereto at the same temperature and stirring was performed for a certain period of time while dissolving the monomer. Thereafter, DMPA was added so that a solid concentration was 13 wt %, thereby preparing a polyimide precursor solution 4. The polyimide precursor solution 4 had a viscosity of 4,300 cp.

Preparation Example 5

TFMB (0.999)/Example 2 (0.2)/PMDA (0.8), unit: mole ratio
A container with a stirrer in which a nitrogen stream flows was filled with 180 g of N,N-dimethylpropionamide (DMPA), and then 18.33 g of 2,2'-bis(trifluoromethyl)-4,4'-biphenyl diamine (TFMB) was dissolved in the state in which the temperature of the reactor was maintained at 25° C. 5.96 g of a novel monomer 2 (Example 2, Material J) and 10 g of pyromellitic dianhydride (PMDA) were added thereto at the same temperature and stirring was performed for a certain period of time while dissolving the monomer. Thereafter, DMPA was added so that a solid concentration was 13 wt %, thereby preparing a polyimide precursor solution 5. The polyimide precursor solution 5 had a viscosity of 5,200 cp.

Preparation Example 6

TFMB (0.999)/Example 3 (0.2)/PMDA (0.8), unit: mole ratio
A container with a stirrer in which a nitrogen stream flows was filled with 179 g of N,N-dimethylpropionamide (DMPA), and then 18.33 g of 2,2'-bis(trifluoromethyl)-4,4'-biphenyl diamine (TFMB) was dissolved in the state in which the temperature of the reactor was maintained at 25° C. 5.87 g of a novel monomer 3 (Example 3, Material M) and 10 g of pyromellitic dianhydride (PMDA) were added thereto at the same temperature and stirring was performed for a certain period of time while dissolving the monomer. Thereafter, DMPA was added so that a solid concentration was 13 wt %, thereby preparing a polyimide precursor solution 6. The polyimide precursor solution 6 had a viscosity of 5,200 cp.

Comparative Preparation Example 1

TFMB (0.999)/BPAF (1.0), unit: mole ratio
A container with a stirrer in which a nitrogen stream flows was filled with 173 g of N,N-dimethylpropionamide (DMPA), and then 13.96 g of 2,2'-bis(trifluoromethyl)-4,4'-biphenyl diamine (TFMB) was dissolved in the state in which the temperature of the reactor was maintained at 25° C. 20 g of 9,9'-bis(3,4-dicaroxyphenyl)fluorene dianhydride (BPAF) was added thereto at the same temperature and stirring was performed while dissolving the compound for a certain period of time. Thereafter, DMPA was added so that a solid concentration was 13 wt %, thereby preparing a polyimide precursor solution A. The polyimide precursor solution A had a viscosity of 4,200 cp.

Comparative Preparation Example 2

TFMB (0.999)/BPAF (0.2)/PMDA (0.8), unit: mole ratio
A container with a stirrer in which a nitrogen stream flows was filled with 175 g of N,N-dimethylpropionamide (DMPA), and then 18.33 g of 2,2'-bis(trifluoromethyl)-4,4'-biphenyl diamine (TFMB) was dissolved in the state in which the temperature of the reactor was maintained at 25° C. 5.25 g of 9,9'-bis(3,4-dicaroxyphenyl)fluorene dianhydride (BPAF) and 10 g of pyromellitic dianhydride (PMDA) were added thereto at the same temperature and stirring was performed while dissolving the compound for a certain period of time. Thereafter, DMPA was added so that a solid concentration was 13 wt %, thereby preparing a polyimide precursor solution B. The polyimide precursor solution B had a viscosity of 4,600 cp.

(Preparation of Polyimide Film)
Each of the polyimide precursor solutions of Preparation Examples 1 to 6 and Comparative Preparation Examples 1 and 2 was spin-coated on a glass substrate. The glass substrate on which the polyimide precursor solution was coated was placed in an oven, heated at a rate of 4° C./min, and maintained at 80° C. for 30 minutes, at 220° C. for 30 minutes, and at 450° C. for 1 hour to proceed with a curing process. After completing the curing process, the glass substrate was immersed in water to form a film on the glass substrate, and the film was detached and dried in an oven at 100° C. to prepare a polyimide film.

The physical properties of the polyimide film prepared by the above method were measured by the above evaluation methods, and are shown in the following Table 1:

TABLE 1

| Item | unit | Preparation Example 1 | Preparation Example 2 | Preparation Example 3 | Preparation Example 4 | Preparation Example 5 | Preparation Example 6 | Comparative Preparation Example 1 | Comparative Preparation Example 2 |
|---|---|---|---|---|---|---|---|---|---|
| Thickness | um | 10 | 10 | 10 | 10 | 10 | 10 | 10 | 10 |
| Sol. Con. | wt % | 10.5 | 10.3 | 11.8 | 11.2 | 10.2 | 10.3 | 13.5 | 10.5 |
| Viscosity | cps | 4500 | 5200 | 4200 | 4300 | 5200 | 5200 | 4200 | 4600 |
| Tg | ° C. | N.D. | N.D. | N.D. | 450 | N.D. | N.D. | 400 | N.D. |
| Td1 % | ° C. | 560 | 558 | 553 | 515 | 535 | 510 | 558 | 559 |
| CTE 100~450° C. | ppm/° C. | 35 | 6.5 | 39 | 43 | 7.6 | 8.3 | 55 | 8.9 |

TABLE 1-continued

| Item | unit | Preparation Example 1 | Preparation Example 2 | Preparation Example 3 | Preparation Example 4 | Preparation Example 5 | Preparation Example 6 | Comparative Preparation Example 1 | Comparative Preparation Example 2 |
|---|---|---|---|---|---|---|---|---|---|
| Total light transmittance | % | 88 | 87 | 90 | 88 | 88 | 88 | 88 | 87 |
| YI | — | 7.5 | 10.8 | 7.2 | 7.5 | 7.4 | 7.8 | 6.5 | 10.3 |
| Haze | % | 0.2 | 0.1 | 0.1 | 0.1 | 0.1 | 0.1 | 0.1 | 0.2 |
| Modulus | GPa | 6.8 | 7.5 | 6.5 | 6.1 | 7.2 | 7.1 | 5.9 | 6.8 |
| Elongation | % | 20 | 25 | 27 | 15 | 29 | 23 | 13 | 15 |
| C.R. test (Stripper & Developer) | — | ○ | ○ | ○ | Δ | ○ | ○ | Δ | ○ |

As shown in the above Table 1, in Preparation Examples 1, 3, and 4 which were polyimide films derived from the tetracarboxylic acid dianhydride according to the present invention, a coefficient of thermal expansion was 35-43 ppm/° C., a haze was 0.1 to 0.2, a yellow index (YI) was 7.2 to 7.5, a total light transmittance was 88 to 90%, a modulus was 6.1 to 6.8, and an elongation was 15 to 27%, and the characteristics for each item were measured at a similar level.

In addition, in Preparation Examples 2, 5, and 6 which were polyimide films further including a repeating unit derived from pyromellitic dianhydride (PMDA), a coefficient of thermal expansion was 6.5 to 8.3 ppm/° C., a haze was 0.1, a yellow index (YI) was 7.4 to 10.8, a total light transmittance was 87 to 88%, a modulus was 7.1 to 7.5, and an elongation was 23 to 29%, and the characteristics for each item were measured at a similar level.

The effects as such were thermal resistance, optical properties, and mechanical properties which were significantly improved as compared with Comparative Preparation Example 1 or 2.

A polyimide film prepared by the novel tetracarboxylic acid dianhydride according to an exemplary embodiment of the present invention has high transparency and thermal resistance and has excellent thermal dimensional stability due to a substrate of which the stress is not increased even with a heat treatment at a high temperature. In particular, the tetracarboxylic acid dianhydride according to an exemplary embodiment of the present invention may form a rigid chemical structure, which may increase linearity of a polyimide main chain. Due to the structural characteristic, a lower coefficient of linear thermal expansion may be satisfied.

In addition, the tetracarboxylic acid dianhydride according to an exemplary embodiment of the present invention may decrease intramolecular and intermolecular interactions due to a decrease in optical anisotropy. Therefore, the present invention may be optically very good and implement uniform transmittance to total light rays.

According to an exemplary embodiment of the present invention, a colorless transparent polyimide film having excellent thermal dimensional stability may be provided. In addition, the polyimide film according to an exemplary embodiment of the present invention may have excellent mechanical strength and flexibility as well as excellent thermal resistance. Thus, the present invention may be useful in various fields such as a device substrate, a flexible display substrate, an optical film, an integrated circuit (IC) package, an adhesive film, a multilayer flexible printed circuit (FPC), a tape, a touch panel, and a protective film for an optical disc.

Specifically, the polyimide film according to the present invention i) may satisfy a coefficient of thermal expansion (CTE) of 50 ppm/° C. or less at 100 to 450° C., ii) may have YI in accordance with ASTM E313 of 15 or less, a haze in accordance with ASTM D1003 of 2 or less, and a total light transmittance in a 380 to 780 nm section in accordance with ASTM D1746 of 80% or more, iii) may have a modulus in accordance with ASTM D882 of 8.0 or less and an elongation of 15% or more, or may satisfy these properties at the same time.

Hereinabove, although the present invention has been described by specified matters and specific exemplary embodiments, they have been provided only for assisting in the entire understanding of the present invention. Therefore, the present invention is not limited to the exemplary embodiments, and various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

What is claimed is:

1. A tetracarboxylic acid dianhydride represented by the following Chemical Formula 1:

[Chemical Formula 1]

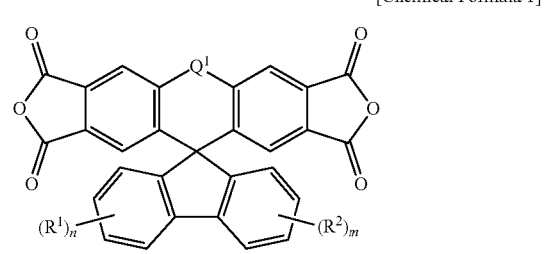

wherein $Q^1$ is a single bond, —C(=O)—, —C(=O)O—, —C(=O)NH—, —NR'—, —S—, —SO$_2$—, —CH$_2$—, or a combination thereof, wherein R' is hydrogen or C1-C10 alkyl;

$R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent to form a ring; and n and m are independently of each other an integer selected from 0 to 4, and when n and m are an integer of 2 or more, $R^1$ and $R^2$ may be the same as or different from each other.

2. The tetracarboxylic acid dianhydride of claim 1, wherein the tetracarboxylic acid dianhydride is a compound represented by the following Chemical Formula 2:

[Chemical Formula 2]

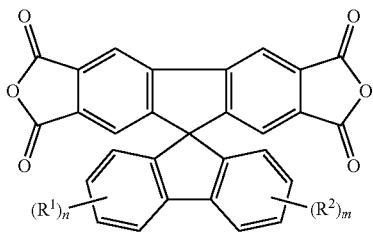

wherein
$R^1$, $R^2$, n, and m are as defined in Chemical Formula 1 of claim 1.

3. The tetracarboxylic acid dianhydride of claim 1, wherein the tetracarboxylic acid dianhydride is selected from compounds represented by the following Chemical Formulae 3 to 5:

[Chemical Formula 3]

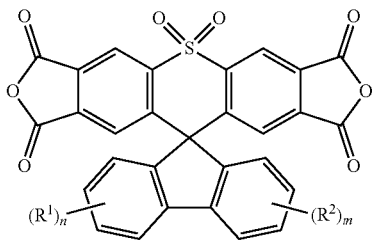

[Chemical Formula 4]

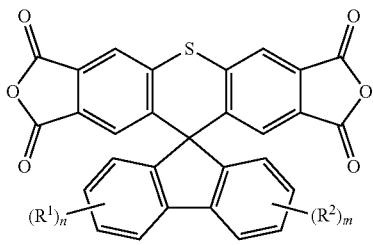

[Chemical Formula 5]

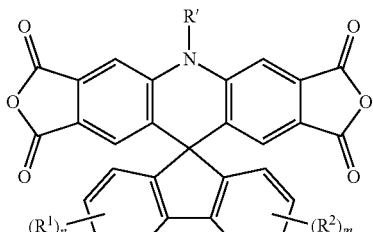

wherein
$R^1$, $R^2$, R', n, and m are as defined in Chemical Formula 1 of claim 1.

4. The tetracarboxylic acid dianhydride of claim 1, wherein in Chemical Formula 1, $R^1$ and $R^2$ are independently of each other a halogen, hydroxy, thiol, nitro, cyano, C1-C10 alkyl, C1-C10 alkoxy, C6-C20 aryl, C1-C10 haloalkyl, or C1-C10 haloalkoxy, and n and m are independently of each other an integer selected from 0 to 2.

5. The tetracarboxylic acid dianhydride of claim 1, wherein in Chemical Formula 1, $R^1$ and $R^2$ are independently of each other a halogen, hydroxy, thiol, nitro, cyano, C1-C4 alkyl, C1-C4 alkoxy, C6-C18 aryl, C1-C4 haloalkyl, or C1-C4 haloalkoxy, and n and m are independently of each other an integer selected from 0 to 2.

6. The tetracarboxylic acid dianhydride of claim 1, wherein in Chemical Formula 1, $R^1$ and $R^2$ are independently of each other a halogen, nitro, cyano, C1-C4 alkyl, C1-C4 alkoxy, C6-C12 aryl, C1-C4 haloalkyl, or C1-C4 haloalkoxy, and n and m are independently of each other an integer selected from 0 to 2 and satisfy 0≤n+m≤2.

7. The tetracarboxylic acid dianhydride of claim 1, wherein the tetracarboxylic acid dianhydride are at least one compound selected from the following structures:

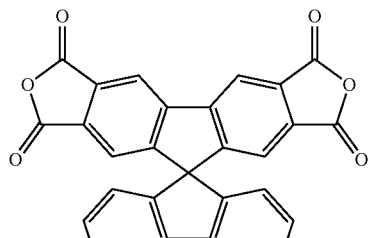

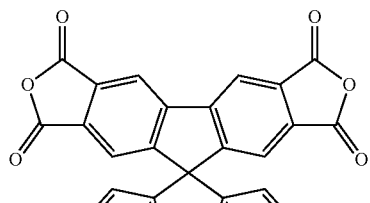

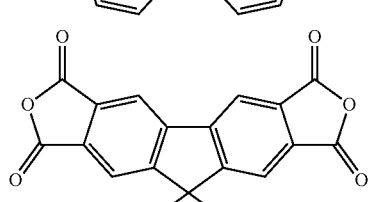

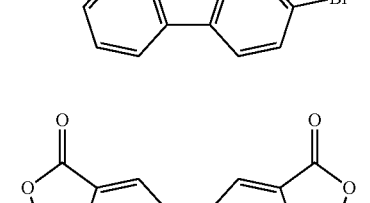

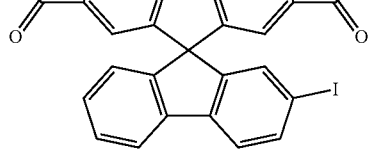

-continued
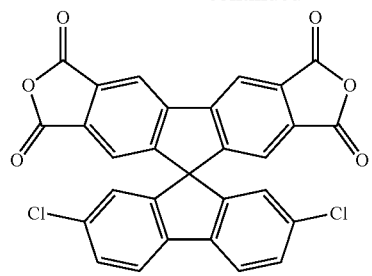
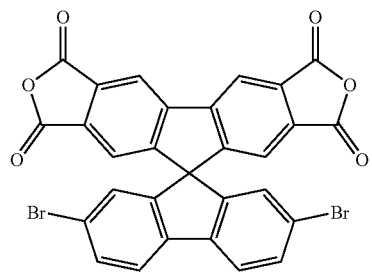
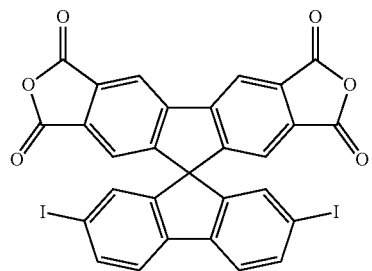
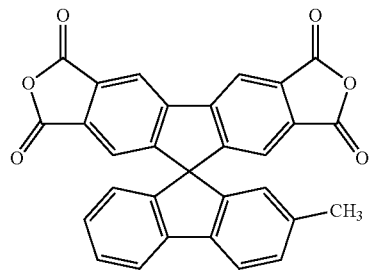
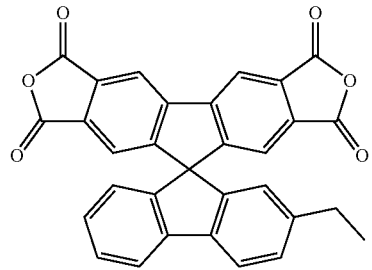
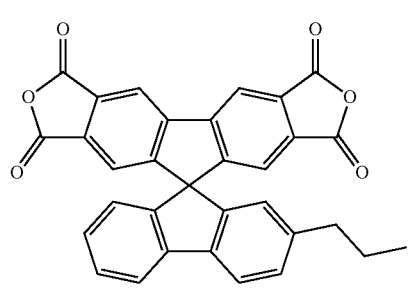
-continued
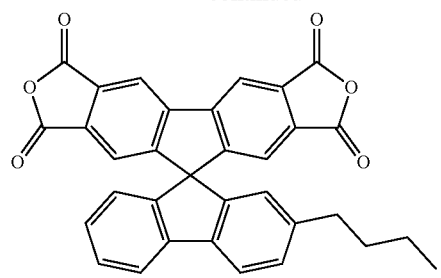
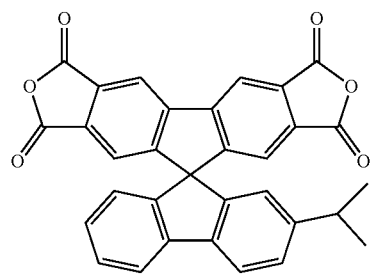
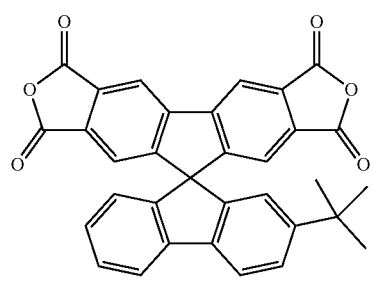
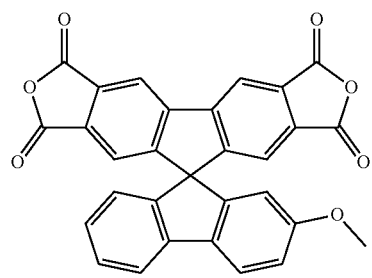
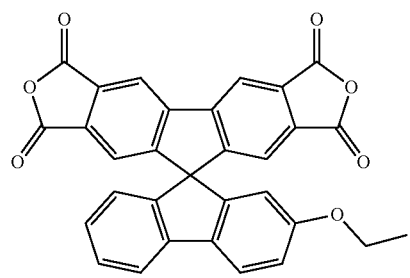
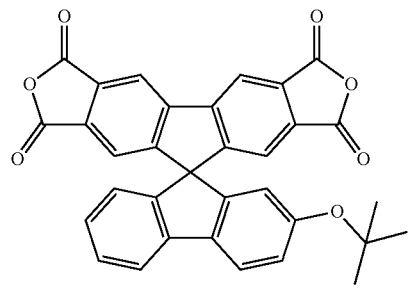

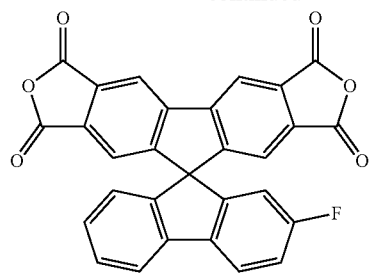
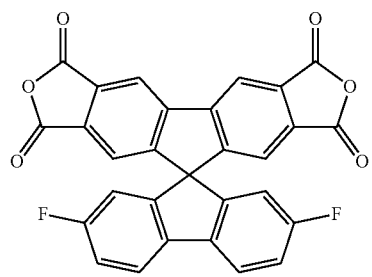
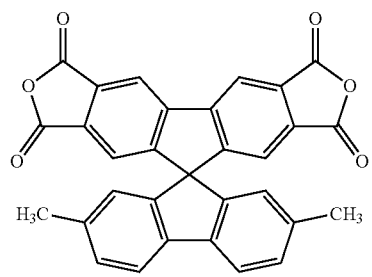
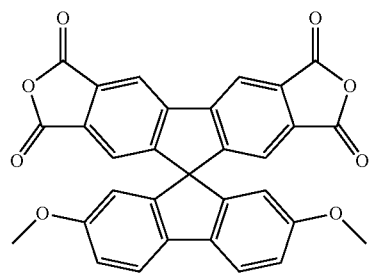
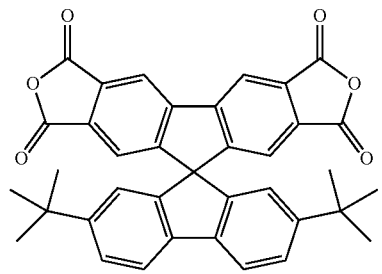
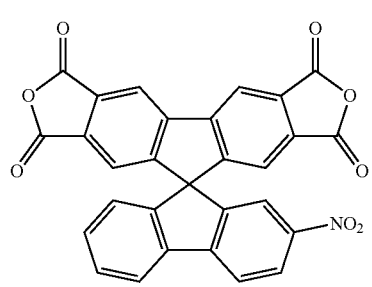
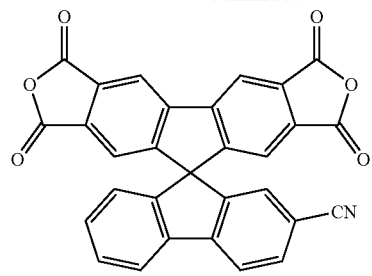
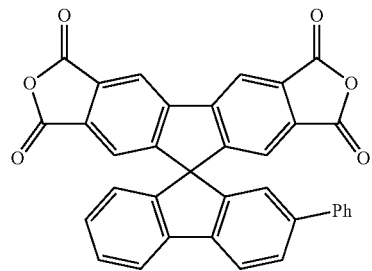
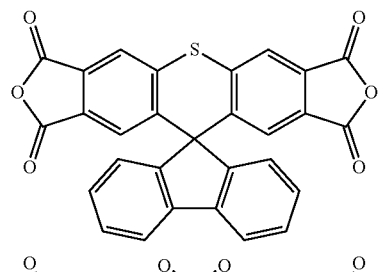
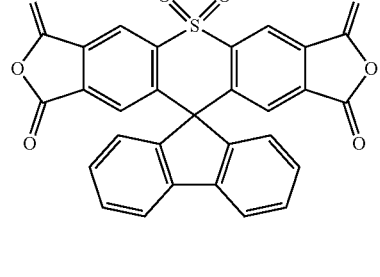
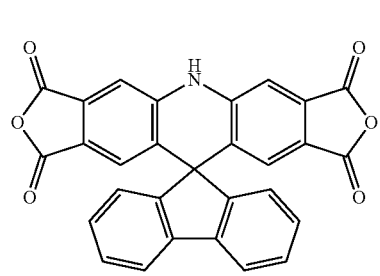
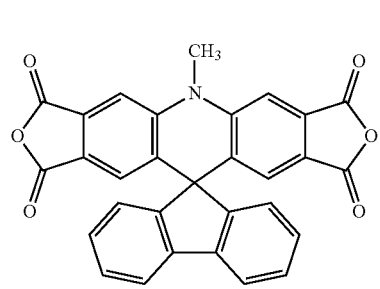

-continued

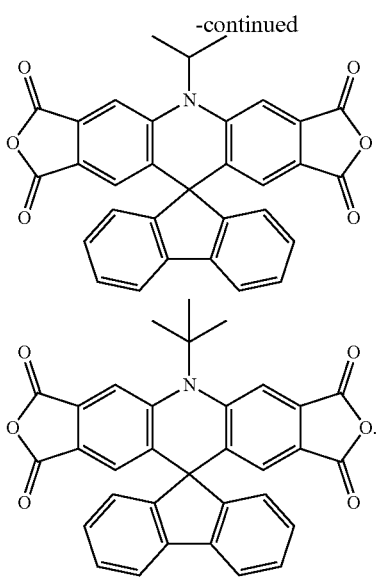

8. A method for preparing a tetracarboxylic acid dianhydride represented by the following Chemical Formula 1, the method comprising: dehydrating and cyclizing a compound represented by the following Chemical Formula A in the presence of a dehydrating agent:

[Chemical Formula A]

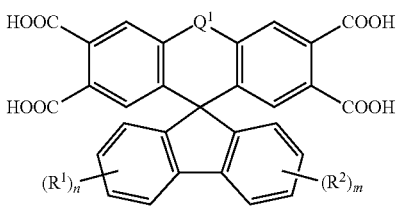

-continued

[Chemical Formula 1]

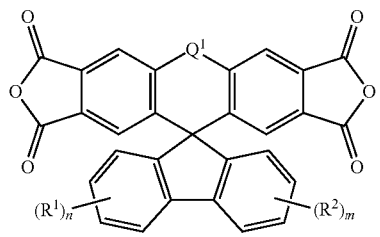

wherein $Q^1$ is a single bond, —C(=O)—, —C(=O)O—, —C(=O)NH—, —NR'—, —S—, —SO$_2$—, —CH$_2$—, or a combination thereof, wherein R' is hydrogen or C1-C10 alkyl;

$R^1$ and $R^2$ are independently of each other a halogen, hydroxy, thiol, nitro, cyano, C1-C10 alkyl, C1-C10 alkoxy, C6-C20 aryl, or a combination thereof, or may be connected to an adjacent substituent to form a ring; and n and m are independently of each other an integer selected from 0 to 4, and when n and m are an integer of 2 or more, $R^1$ and $R^2$ may be the same as or different from each other.

9. The method for preparing a tetracarboxylic acid dianhydride of claim 8, wherein the dehydrating agent is an acid anhydride.

10. A composition comprising the tetracarboxylic acid dianhydride of claim 1.

11. The composition of claim 10, further comprising: an organic solvent.

12. The composition of claim 11, wherein the tetracarboxylic acid dianhydride is comprised at 1 to 30 wt %, based on a total weight.

* * * * *